(12) United States Patent
Sullivan

(10) Patent No.: US 7,197,492 B2
(45) Date of Patent: Mar. 27, 2007

(54) COMPUTERIZED RISK MANAGEMENT MODULE FOR MEDICAL DIAGNOSIS

(76) Inventor: Daniel Joseph Sullivan, 2000 Spring Rd., Suite 200, Oak Brook, IL (US) 60523

( * ) Notice: Subject to any disclaimer, the term of this patent is extended or adjusted under 35 U.S.C. 154(b) by 0 days.

(21) Appl. No.: 10/000,879

(22) Filed: Nov. 2, 2001

(65) Prior Publication Data

US 2002/0077865 A1  Jun. 20, 2002

Related U.S. Application Data

(60) Provisional application No. 60/245,255, filed on Nov. 2, 2000.

(51) Int. Cl.
    *G06F 7/00* (2006.01)
(52) U.S. Cl. .............. 707/2; 705/2; 600/301
(58) Field of Classification Search .............. 707/2, 707/104.1, 1, 3; 705/2, 3; 600/300, 301
    See application file for complete search history.

(56) References Cited

U.S. PATENT DOCUMENTS

| | | | |
|---|---|---|---|
| 5,471,382 A | | 11/1995 | Tallman et al. |
| 5,673,691 A | * | 10/1997 | Abrams et al. ............ 600/300 |
| 5,764,913 A | * | 6/1998 | Jancke et al. ............... 345/764 |
| 5,832,448 A | * | 11/1998 | Brown ........................... 705/2 |
| 5,845,253 A | | 12/1998 | Rensimer et al. |
| 5,845,255 A | * | 12/1998 | Mayaud ......................... 705/3 |
| 5,921,920 A | * | 7/1999 | Marshall et al. ............ 600/300 |
| 5,942,986 A | | 8/1999 | Shabot et al. |
| 6,005,571 A | * | 12/1999 | Pachauri ..................... 345/764 |
| 6,106,459 A | * | 8/2000 | Clawson ..................... 600/300 |
| 6,126,596 A | | 10/2000 | Freedman |
| 6,161,095 A | * | 12/2000 | Brown ........................... 705/2 |
| 6,190,313 B1 | * | 2/2001 | Hinkle ........................ 600/300 |
| 6,322,502 B1 | * | 11/2001 | Schoenberg et al. ........ 600/300 |
| 7,108,635 B2 | * | 9/2006 | Herren et al. ............... 600/300 |

OTHER PUBLICATIONS

Diagnostic and Statistical Manual of Mental Disorders, Fourth Edition ("DMS-IV"), American Psychiatric Association, printed May 16, 2006, from internet website address http://allpsych.com/disorders/dsm.html, 2 pages.

* cited by examiner

*Primary Examiner*—Sam Rimell
(74) *Attorney, Agent, or Firm*—Patzik, Frank & Samotny Ltd.

(57) ABSTRACT

Apparatus and a method are provided for improving the medical care of patients. The apparatus includes an input device, a medical risk database, a data processor, and a communication device. Data entered in the input device, usually by a health care professional, defines a patient data record. The medical risk database associates certain patient data entered into the data record, which increases the risk of a missed medical care opportunity, with additional medical care to address the risk. The communication device responds to the identification of patient data presenting a medical risk by communicating to a health care professional additional medical care selected to identify and take advantage of a medical care opportunity.

59 Claims, 23 Drawing Sheets

DON'T GET BURNED : 3.5 PAIN RADIATING TO THE BACK

RECOMMENDATION:
CONSIDER THE DIAGNOSIS OF THORACIC AORTIC DISECTION.
- ○ MEASURE BILATERAL ARM BLOOD PRESSURE, IF POSSIBLE.
- ○ LOOK AT THE X-RAY SPECIFICALLY FOR SIGNS OF TAD (E.G. ABNORMAL AORTIC CONTOUR, WIDENING OR MEDIASTINUM, DEVIATION OF THE TRACHEA OR MAINSTEM BRONCHI). DOCUMENT YOUR OBSERVATIONS.

THIS IS OFFERED AS A GENERAL RECOMMENDATION, NOT A STANDARD OF CARE. SPECIFIC MANAGEMENT IS SUBJECT TO THE FACTS OF A PARTICULAR PATIENT'S PRESENTATION AND THE INDIVIDUAL PHYSICIAN'S JUDGEMENT.

INGALLS MEMORIAL HOSPITAL – DAN SULLIVAN, MD
CHEST PAIN CHART

| BACK | MY PATIENTS | MAIN |

| PATIENT | KENNETH BROWDER | AGE | M21 | COMPLAINT | ABDOMINAL PAIN, BACK PAIN |
|---|---|---|---|---|---|
| DISPOSITION | ADMISSION | ACUITY | | COMMENT | |

HPI–(HCFA) LEVEL I–III = 1–3 items, Level IV–V=4+ Items

| CHIEF COMPLAINT | CHEST PAIN: ▽ SOB: ▽ NAUSEA: ▽ VOMITING: ▽ DIAPHORESIS: ▽ |
| | PALPITATIONS ▽ AICD EVENT: ▽ PATIENT OVER 40 YEARS OF AGE? ▽ |

| TIME COURSE | ○ ONSET ○ SUDDEN ○ GRADUAL □ RESOLVED | □ CONSTANT □ INTERMITTENT □ WORSE/PERSISTENT |

| LOCATION | ○ □ NO LOCALIZING Sx. MOST SEVERE IN: ▽ | RADIATION: NONE TO BACK ▽ ○ |

| CHIEF COMPLAINT | CHEST PAIN: ▽ SOB: ▽ NAUSEA: ▽ VOMITING: ▽ DIAPHORESIS: ▽ |
| --- | --- |
| | PALPITATIONS ▽ AICD EVENT: ▽ PATIENT OVER 40 YEARS OF AGE? ▽ |

HPI–(HCFA) LEVEL I–III = 1–3 Items, Level IV–V=4+ Items

| TIME COURSE | ONSET SUDDEN GRADUAL RESOLVED ☐CONSTANT ☐INTERMITTENT ☐WORSE/PERSISTENT |
| --- | --- |
| LOCATION | ☐NO LOCALIZING Sx MOST SEVERE IN: ▽ RADIATION: NONE TO BACK |

| EXACERBATED BY | ☐ EXERCISE ☐ PALPATATION OF CHEST ☐ MOVEMENT/WALKING ☐ COUGH/ DEEP BREATH ☐ OTHER ☐ NOTHING |
|---|---|
| RELIEVED BY | NITRO: ▽ ☐ OXYGEN ☐ SUPINE/UPRIGHT ☐ REMAINING STILL ☐ OTC MEDICATIONS ☐ FOOD ☐ NOTHING |
| RISK FACTORS | ○ CAD RISK / NONE / KNOWN CAD  ○ TAD RISK / NONE / HYPERTENSION  ○ PE RISK / NONE / SMOKING |
| OTHER: | E/M CAVEAT: ▽ |
| EXTRA NOTES SPACE (EHS) | |

EXTREMITY EXAM

☐ NORMAL INSPECTION
☐ ROT. CUFF NONTENDER
☐ BICEPS NONTENDER
☐ ROM NORMAL
☐ LIGAMENTS STABLE
☐ AC JOINT NONTENDER
☐ NO ECCHYMOSIS, ABRASION OR LACERATION
☐ AXILLARY NERVE NORMAL
☐ CAPILLARY REFILL NORMAL
☐ PULSES INTACT DISTALLY
☐ MOTOR INTACT DISTALLY
☐ SENSORY INTACT DISTALLY
☐ ALL OF THE ABOVE ARE NORMAL

ECHYMOSIS: DIFFUSE ANTERIOR
TENDERNESS: DIFFUSE G-H JOINT
☐ AXILLARY NERVE INJURY
☐ CAPILLARY REFILL DELAYED
☐ DISTAL PULSE ABNORMALITY
☐ MOTOR ABNORMALITY
☐ SENSORY ABNORMALITY
☐ JOINT UNSTABLE
☐ DEFORMITY ON INSPECTION
OTHER: TENTING OF SKIN DISTAL PULSES POOR

☐ PERRL
☐ SCLERA NOT INJECTED

PUPILS: SCLERA: CONJUNCTIVA:

| BED | PATIENT | AGE | COMPLAINT | MD | RN | ORDERS | DONE | COMMENT | LOS | RN TIME |
|---|---|---|---|---|---|---|---|---|---|---|
| ○ WAITING | DAVY CROCKETT | 51 | ACUTE SUICIDE/HOMICIDE RISK | DD | | * | | --- | 1:00 | :01 |
| ○ WAITING | JIM GEORGE | 40 | CARDIAC: CHEST PAIN | DD | | * | C | --- | :55 | :06 |
| ○ WAITING | BILL BRADLEY | 58 | DIARRHEA | DD | | * | | --- | :24 | :37 |

PATIENT FLOW
PATIENT INFORMATION
ADMINISTRATION

TRIAGE | TRANSFER- | ▽ DISPOSITION
ENTER: | ▽ DISPLAY
MY PATIENTS | PULSE CHECK | ADMIN | HELP | LOGOUT

*FIG. 19*

IBEX HOSPITAL – DOCTOR DAN
IBEX DISPOSITION

| PATIENT | CLINTON WILLIAM J | AGE | M59 | COMPLAINT | HEADACHE |
|---------|-------------------|-----|-----|-----------|----------|
| SOURCE  |                   | ACUITY | | COMMENT | |
| BP      | PULSE             | RESP | TEMP | PAIN | ENTRY |
| 140/80  |                   | 18 | 100.4 | 3 | NT 13:51 |

128

PROBLEM
THE PULSE (140) FOR THIS PATIENT IS SEVERELY ABOVE NORMAL. (50-100)   NORMAL RANGE

KNOWN ALLERGIES

| | |
|---|---|
| MAY 30 2001 16:29 DD | PENICILLIN |

| WRITE PRESCRIPTION | | DISPENSE | QUANTITY | UNIT | SCHEDULE | REMOVE |
|---|---|---|---|---|---|---|
| ☐ | BIAXIN : TABLET : 500 MG : ORAL | 1 | 1 | 20 | BID | ☐ |
| ☐ | CIPRO : TABLET : 500 MG : ORAL | 20 | 20 | 1 | BID | ☐ |
| ☐ | COUMADIN : TABLET : 10 MG : ORAL | 20 | 20 | 1 | QD | ☐ |
| | KEFLEX : CAPSULE MONOHYDRATE : 500 MG : ORAL ALLERGY INTERACTION : PENICILLIN | 40 | 40 | 1 | QID | ☐ |
| | PEN-V : TABLET : V POTASSIUM 250 MG : ORAL ALLERGY INTERACTION : PENICILLIN | 40 | 40 | 1 | QID | ☐ |
| ☐ | TORADOL : TABLET : 10 MG : ORAL | 30 | 30 | 1 | TID | ☐ |
| ☐ | TYLENOL : TABLET : 500 MG : ORAL | 50 | 50 | 1 | Q4-6H | ☐ |

FIG. 23
(PRIOR ART)

COMPUTERIZED RISK MANAGEMENT MODULE FOR MEDICAL DIAGNOSIS

This application claims the benefit of U.S. Provisional Application No. 60/245,255, filed Nov. 2, 2000.

FIELD OF THE INVENTION

This invention generally relates to apparatus and methods for improving medical care. ("Medical care" is broadly defined here to include both medical diagnosis and therapeutic treatment of a patient.) This invention relates more particularly to such apparatus and methods that can be used by a health care professional to avoid making the kinds of professional mistakes that can lead to a significant risk of medical errors, patient injury and legal liability.

BACKGROUND OF THE INVENTION

"Health care professionals" is used broadly here to refer to anyone who participates in the diagnosis or treatment of medical problems. For example, medical doctors, dentists, nurses, nurse-practitioners, medical technologists, physical therapists, and other health workers that assist in examination of patients, diagnosis, or treatment are all included by this term.

A health care professional diagnoses an illness by collecting and evaluating information about the patient, then determining what disease or condition best fits the information. The information gathered from the patient usually is processed to reach a diagnosis by using a protocol learned during the professional's professional training and modified and updated by his or her medical experience. The protocol is an ordered process by which a health care professional ascertains information that allows the professional to rule out possible diseases until enough information is gathered to eliminate all but the diagnosed condition. Alternatively, the protocol may end when an appropriate treatment is identified. Recently, medical associations, health maintenance organizations, and hospitals, among others, have prescribed protocols. Employed health care professionals in particular are often subject to mandated protocols.

One problem in the field of medicine is how to improve diagnostic protocols to take into account advances in medical knowledge. A related problem is how to ensure that health care professionals update their skills to take advantage of advances in medical knowledge. Still another problem is how to expedite the diagnosis and treatment of certain conditions that should be treated quickly, so treatment can begin soon enough to be most effective.

U.S. Pat. No. 6,095,973 discloses a data processing system and method for evaluating the treatment of chest pain patients in a medical facility.

U.S. Pat. No. 6,029,138 discloses a decision support system for the selection of a diagnostic test or therapeutic intervention, which are both called "studies" in that patent.

U.S. Pat. No. 4,857,713 discloses a program for reducing hospital errors in the delivery of medications, goods, services or procedures in patient treatment.

U.S. Pat. No. 5,732,397 describes an automated system for use in decision-making processes, which is said to improve the quality and consistency of decisions made.

U.S. Pat. No. 5,772,585 discloses a common user interface to allow different medical personnel access to centralized files regarding patients.

U.S. Pat. No. 5,832,450 describes an electronic medical record system that stores data about individual patient encounters in a convenient form.

U.S. Pat. No. 5,845,255 describes an electronic prescription creation system for physician use that includes an adverse indication review and online access to comprehensive drug information including scientific literature.

U.S. Pat. No. 5,911,132 discloses diagnosing and treating patient diseases using a epidemiological database containing medical, personal or epidemiological data relevant to a presented set of symptoms, test results, a diagnosis, etc.

U.S. Pat. No. 5,915,240 discloses a context-sensitive medical lookup reference computer system for accessing medical information over a network.

U.S. Pat. No. 5,924,074 discloses a medical records system that is said to create and maintain all patient data electronically.

U.S. Pat. No. 5,953,704 discloses a system in which a user inputs information related to the health condition of an individual.

U.S. Pat. No. 6,022,315 discloses a system and method for providing computerized, knowledge-based medical diagnostic and treatment advice to the general public over a telephone network or a computer network.

There is currently a need in the medical field for a system that communicates to a health care professional carrying out a diagnosis that a certain symptom, combination of symptoms, or other patient information recorded by the physician is associated with an increased risk of a missed medical care opportunity leading to a less favorable patient outcome. (A "medical care opportunity" is defined as an opportunity to correctly or more quickly diagnose or treat the patient's condition and thus provide a better patient outcome.) Further, there is also a need in the medical field for a system communicating to the health care professional special steps to take to avoid the missed medical care opportunity.

BRIEF SUMMARY OF THE INVENTION

One aspect of the invention is an apparatus for improving the medical care of patients. The apparatus includes an input device, a medical risk database, a data processor, and a communication device.

The input device can be any device that is useful for entering medical data relating to a patient. Data entered in the input device defines a patient data record.

The medical risk database associates certain patient data, which increases the of a missed medical care opportunity, with additional medical care. The additional medical care is a predetermined action that reduces the risk of a missed medical care opportunity, despite the presentation of the patient data.

The data processor is programmed to compare the patient data record with the medical risk database. This comparison is carried out to identify patient data in the record that increases the risk of a missed medical care opportunity.

The communication device responds to the identification of patient data that increases the risk of a missed medical care opportunity. The communication device responds by communicating to a health care professional additional medical care. The additional medical care is selected to reduce the risk of a missed medical care opportunity.

Another aspect of the invention is an interactive method a health care professional can use for avoiding medical risk while the health care professional is providing medical care to a patient.

The health care professional records medical data presented by the patient in a data storage device, forming data records.

The health care professional has access to a medical risk database maintained on a data storage medium. The database associates certain medical data with additional medical care. The certain medical data is data that increases the risk of a missed medical care opportunity. The additional medical care is something that can be done to reduce the risk of a missed medical care opportunity, despite the presentation of the certain medical data.

A data processor is used to compare the medical data presented by the patient with the medical data in the medical risk database to identify whether medical data presented by the patient is associated with a risk of missed medical care opportunity.

If medical information presented by the patient is associated with a risk of missed medical care opportunity, information about additional medical care that would reduce the risk of a missed medical care opportunity is presented to the health care professional.

Another aspect of the invention is a red-light, green-light prompting system that suggests or prompts the health care provider to include the important or critical elements of documentation of a patient's particular medical condition in the medical record. This component of the invention contains some aspects of simple medical logic. For example, the critical elements of documentation for a patient with a laceration are not known until the specific location of the laceration is known. Once the health care provider indicates the location of the laceration, the red-light, green-light prompts then appear at the appropriate locations in the templated medical record. Prompting systems other than a red-light green-light system can be used.

Another aspect of the invention is immediate electronic access to critical information behind a "key information" icon, at various points throughout the many templates. For example in the shoulder injury template, in the physical exam section for the shoulder, there are three key information icons containing the following information: 1) the anatomy of the shoulder; 2) the vascular anatomy of the arm; and 3) the nerve distribution of the arm in a dermatome map. This information is currently available in textbooks, on the Internet, or in policy and protocols. The key information icons make this critical information immediately accessible as the health care provider evaluates the patient and/or creates the medical record.

Another aspect of the program is the use of the red-light green-light system, and a drop down list of acute life threatening emergencies, utilized by the triage nurse to identify, expedite and prioritize patients with these special conditions. Accordingly, in the triage situation, a warning about the high-risk diagnosis is indicated. This part of the invention also contains a special warning to notify the physician and charge nurse in the emergency department. This red-light green-light system also provides mandatory notification of the existence of a second-to-minutes type emergency to the attending physician or attending nurse. Other types of prompting or warning systems may be used.

BRIEF DESCRIPTION OF THE DRAWINGS

Other objects and advantages of the invention will become apparent upon reading the following detailed description and upon reference to the drawings in which:

FIG. 2 shows a portion of an exemplary medical diagnostic template for use with the system of FIG. 1 when diagnosing chest pain.

FIG. 3 is similar to FIG. 2, but shows the template modified to display an activated medical risk icon when an entry is made on the template that the patient has chest pain radiating to the back.

FIG. 4 is a pop-up legend presented by the system when the activated medical risk icon is queried to determine the nature of the medical risk.

FIG. 5 is an illustration of a screen display of the chest pain electronic medical record template with the red-light, green-light prompts all red.

Figure 6:
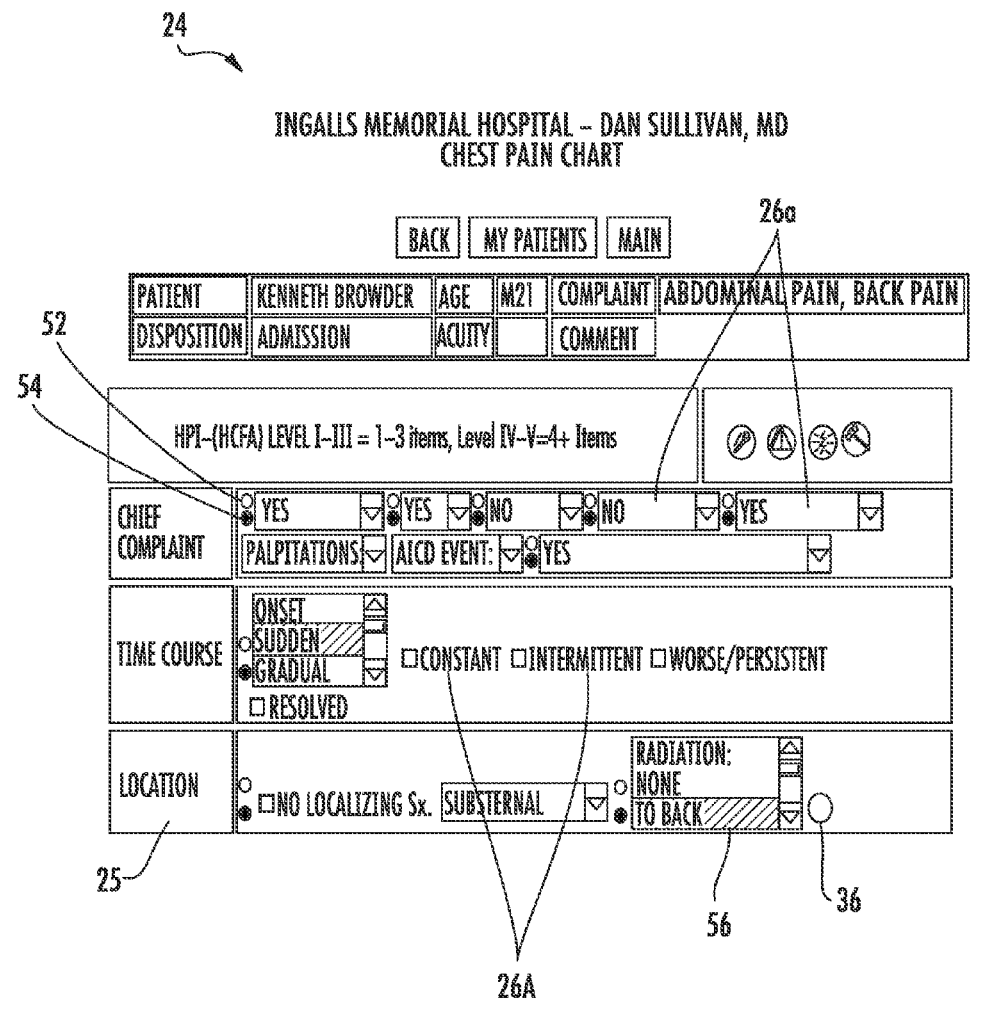

FIG. 6 is an illustration of a screen display of the chest pain electronic medical record template with the red-light, green-light prompts all turned green.

FIG. 7 is another illustration of a screen display of the chest pain electronic medical record template.

FIG. 9 is yet another illustration of a screen display of the chest pain electronic medical record template wherein the user has selected "yes" to the query "Patient Over 40 Years of Age?"

FIG. 11 is an illustration of a screen display demonstrating the use of the red-light, green light system to prompt the practitioner to consider the possible differential diagnosis and risk factors for a particular presentation. This figure shows three of the possible high-risk diagnoses in the chest pain patient on the "Risk Factor" line. These include 1) Coronary Artery Disease (CAD) 2) Thoracic Aortic Dissection (TAD) and 3) Pulmonary Embolism (PE).

FIG. 12 is an illustration of a screen display demonstrating that the practitioner has turned the red-lights green, thus having considered the differential diagnosis.

FIG. 13 is an illustration of a screen display of a template showing the key information icons.

FIG. 15 is an illustration of a screen display of an electronic medical record template showing the possible selections for the "high-risk" query.

FIG. 17 is an illustration of a screen display of an electronic medical record template showing that the triage nurse has completed or "checked" a box associated with a statement indicating that the physician or charge nurse has been notified.

FIG. 19 is another illustration of a screen display of a patient reevaluation template.

FIG. 21 is another illustration of a screen display of a vital sign template showing an example of a warning provided to a discharge nurse or physician during patient disposition.

FIG. 22 is an illustration of a screen display of a prescription medicine template.

FIG. 23 is another illustration of a screen display of a prescription medicine template.

DETAILED DESCRIPTION OF THE INVENTION

Figure 1:
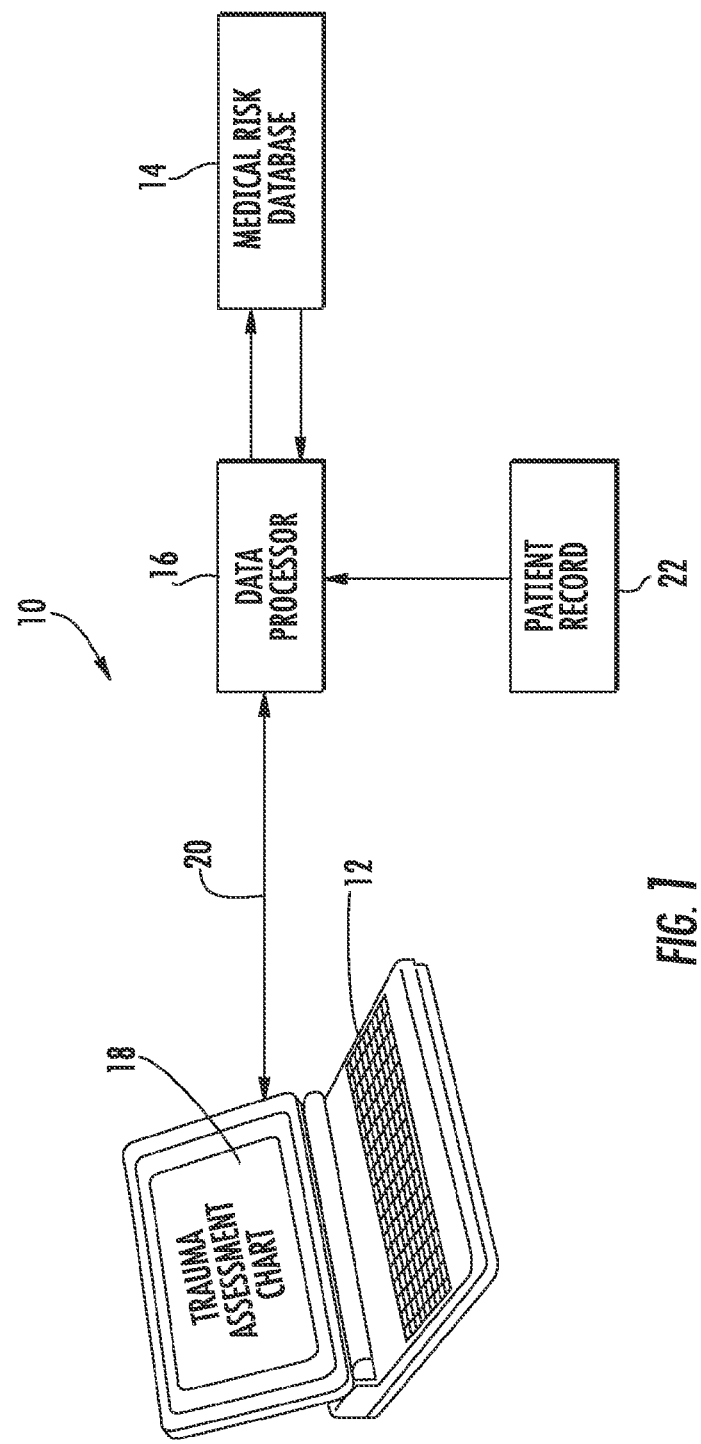
FIG. 1 is a schematic view of one example of a medical charting system suitable for carrying out the present invention.

While the invention will be described in connection with one or more embodiments, it will be understood that the invention is not limited to those embodiments. On the contrary, the invention includes all alternatives, modifications, and equivalents as may be included within the spirit and scope of the appended claims.

The present inventors have discovered a previously overlooked source of information from which appropriate diagnostic protocols can be developed: the results of medical malpractice claims. Each malpractice claim represents a decision made by a patient that his or her medical care was not appropriate and harmed him or her.

For example, a course prepared by inventor Daniel J. Sullivan, M. D., J. D., *High-Risk Acute Care: The Failure to Diagnose* (1998) identifies missed medical diagnoses as the principal cause of most malpractice suits. A missed medical diagnosis is defined here to include either the wrong diagnosis or a delayed diagnosis that leads to a materially worse patient outcome. This conclusion was reached by studying over 1000 medical malpractice suits to determine what caused the alleged malpractice and what could be done to avoid the alleged malpractice. *High-Risk Acute Care: The Failure to Diagnose* (1998) is incorporated herein by reference.

Data about medical malpractice claims has limited scientific value because the data is strongly influenced by non-medical factors. These factors include the differences among the jurors and judges involved in different cases, how credible, worthy, or attractive the plaintiff, the physician, and other parties and witnesses may appear to be, and the skill of the respective lawyers. Other factors include differences in the laws of different states and the common unavailability of data for many claims, particularly claims that are resolved by private settlement instead of by public judgment.

The outcome of cases that proceed to trial depends on whether jurors agree that the care given to the plaintiff that led to the filing of the lawsuit was appropriate.

The amount of damage awarded to a successful plaintiff reflects the jury's impression of how much worse the patient outcome was economically, compared to what it should have been. By putting a dollar value on the harm suffered by the plaintiff, a jury verdict reflects how much importance should be attached to the alleged error in patient care. Again, the medical or scientific communities do not commonly gather this information. It can only be obtained from litigation results.

Despite its limited scientific value, information obtained by studying medical malpractice claims is vitally important to improve diagnostic protocols. Medical malpractice claim experience largely reflects the attitudes of nonscientific, untrained, ordinary people. Such people have no connection with the scientific or medical worlds. The information they provide is not reflected in the usual diagnostic protocols, but often should be.

The present invention is not limited to information derived from medical malpractice claims. Any source of the required information, such as clinical experience, adverse outcomes, medical errors, scientific experimentation, or the opinions of expert health care professionals is contemplated to be useful here.

One embodiment of the invention is the medical charting system 10 shown in FIG. 1. The system 10 generally includes an input device 12, a medical risk database 14, a data processor 16, a communication device 18, and a data link 20.

The input device 12 can be any device that is useful for entering medical data presented by a patient. Data entered in the input device defines a patient data record.

One suitable input device is a cursor-moving device. A cursor moving device can be a pointing device such as a mouse, a track ball, a touch pad, a joystick a voice-activated cursor directing program, a touch screen that moves a cursor responsive to finger or stylus placement or movement on the screen, etc.

Another suitable input device is a text entry device. A text entry device can be a keyboard for directly entering alphanumeric characters or other information directly. A non-alphanumeric keyboard can also be used, for example, a keyboard that has programmed keys directly representing the answers to medical questions indicative of medical information. A text entry device can be a text-generating device that converts spoken or handwritten words or characters into text entries. Two examples of text generating devices are a dictation program and the stylus and tablet of a personal digital assistant. Another suitable text entry device is a scanner for reading or copying alphanumeric text, a bar code, or other indicia.

Another type of input device contemplated here is a mechanism for transmitting data to the system 10 from a medical instrument. Examples of suitable medical instruments are an electrocardiograph, an electroencephalogram (EEG), a blood pressure measuring instrument, a pulse monitor, a thermometer, a laboratory machine, an intravenous drug administration monitor, or any others.

Yet another type of input device contemplated here is a communication device allowing a patient to enter data on his or her own patient record. It is advisable to identify the information so entered as coming from the patient, and to limit access of the patient so only appropriate portions of the patient record, such as the portion input by the patient, can be accessed by the patient, and so pertinent information cannot be erased or changed by the patient after it is entered.

Even another type of input device contemplated here is a magnetic strip reader for extracting information from a card carried by the patient, such as medical information that could be recorded on a patient-carried emergency medical information card or insurance card.

Still another type of input device contemplated here is a communication link between preexisting patient records and the medical charting system 10, as for communicating medical history or previous medical treatment information.

Yet another type of input device contemplated is a communication device adapted to allow for entry of patient information by the attending physician or other medical personnel from the patient's bedside. Such a communication device could be a hand-held computer or the like. It is also contemplated that patient information could be input vocally into the system 10 through a sound input device, such as a microphone or the like, by the attending physician or other medical personnel. Such an embodiment would eliminate the need to input the patient data into the system 10, thereby permitting the physician to treat the patient and input the patient data simultaneously.

The input device is used to input information about a patient. The information is stored as a patient data record 22. Examples are given below of patient record data that is pertinent to determining medical risks.

The patient data record 22 is physically embodied as data stored in any suitable medium. Suitable media include a hard drive, a floppy drive, a tape drive, a magnetic strip (as is often found on a credit card), or any other magnetic medium. Other suitable media include a CD, the internal memory of a computer, information written on paper or in microfiche form (either readable by a computer or by a physician), or in any other form, without limitation. The data in the patient data record 22 can be digital or analog data in text, numerical, graphic, audible, or any other form perceivable by a health care professional.

The patient data record 22 can be physically stored anywhere. For example, the patient data record 22 can be located in a drive of a portable computer, such as a notebook computer or a personal digital assistant, also providing the input device 12, data processor 16, and communication device 18 for the system. This could be a self-contained system carried by a health care professional and used for medical charting. Alternatively, the patient data record 22 can reside in a remote drive, computer, or server, as shown in FIG. 1, and be accessed via a data link 20.

The medical risk database 14 associates certain patient data, which increases the risk of a missed medical care opportunity, with additional medical care. The additional medical care is predetermined action that reduces the risk. Examples of the information in the medical risk database 14 are provided below.

The medical risk database 14 is physically embodied as data stored in any suitable medium. Suitable magnetic media include a hard drive, a floppy drive, a tape drive, a magnetic strip such as the type often found on a credit card, or any other magnetic medium. Other suitable media include a CD, the internal memory of a computer, information recorded in paper or microfiche form (either readable by a computer or by a physician), or in any other form. The data in the medical risk database 14 can be digital or analog data in text, numerical, graphic, audible, or other perceivable form. The media in which the medical risk database and patient data record can be stored can be the same medium or different media. Either of them can be stored in more than one place or in more than one medium. In a simple embodiment, the database 14 can be built into the template 24 shown in FIG. 2 below, so entering certain patient data can prompt the presentation of a message that certain medical action is recommended.

The medical risk database 14 can be physically located anywhere. For example, the medical risk database 14 can be located in a drive of a notebook computer or personal digital assistant also providing the input device 12, data processor 16, and communication device 18 for the system. Alternatively, the medical risk database 14 can reside in a remote drive or computer, as shown in FIG. 1, and be accessed via a data link 20. It likewise can be either network based or Internet based.

The medical risk database 14 can be updated to reflect recent medical or legal experience. The updated database can be updated by providing a subscription CD or Internet download service, by updating a central database that is accessed by many health care professionals, or by any other effective method.

The data processor 16 is programmed to compare the patient data record 22 with the medical risk database 14. This comparison is carried out to identify patient data in the record 22 that increases the risk of a missed medical care opportunity. The data processor 16 can have any suitable form or configuration. It can be a dedicated microprocessor, a programmed general-purpose computer, or any other mechanical or electronic processing device. In a simple form of the system, the data processor can be used simply to update the display to present a communication, responsive to the entry of certain patient data.

The communication device 18 is any type of device that communicates to a health care professional the presence of an increased medical risk, based on the identification by the data processor of information in the patient data record 22 that increases the risk of a missed medical care opportunity. The system 10 responds by communicating to a health care professional proposed additional medical care. The additional medical care is selected to reduce the risk of a missed medical care opportunity.

One suitable embodiment of the communication device 18, illustrated in FIG. 1, is a video display operatively connected to the data processor 16 to visually communicate to the health care professional the presence of an increased medical risk. Another suitable embodiment of the communication device 18 is an alarm providing a signal perceptible to a health care professional. The alarm can be a visible warning, like a symbol on a graphical display or a warning light. The alarm can be an audible warning. The alarm can be a tactile warning, such as a signal sent to a vibrating pager, cellular telephone, or personal digital assistant worn or carried by the health care professional. The alarm can also be presented remotely, as to another health care professional that can attend to the alarm condition. In various embodiments, the alarm can be presented locally only, remotely only, or both locally and remotely.

The alarm can be arranged to ordinarily be selectively perceptible to a health care professional, and not to the patient. For example, it can be presented as a visual display on a terminal screen that is selectively viewable from one angle, presented toward the health care professional, and not from another angle where the patient's eyes are positioned.

The alarm can be encoded, to avoid alarming a patient who happens to encounter it. For example, it can be presented as a non-threatening icon on a visual display or a non-threatening sound. For another example, it can be made to appear or sound like something ordinary in the medical environment, such as an innocuous page on a public address system that is known only to the health care professional to relate to patient data being entered.

The data link 20 can be any means of communication of voice, data, or visual information now known or developed in the future. For example, the link 20 can be a telephone line, an Internet communication pathway (such as a telephone modem link, a dedicated link, a cable modem link, or a satellite link), computer wiring in a hospital or medical office, or any other communication path.

Another aspect of the invention is an interactive method a health care professional can use for avoiding medical risk while the health care professional is providing medical care to a patient. First, the health care professional records medical data presented by the patient in a data storage device, forming a patient data record 22. The health care professional has access to a medical risk database 14 maintained on a data storage medium. The database 14 associates certain medical data in the patient data record 22 with additional medical care. The health care professional uses a data processor 16 to compare the medical data presented by the patient data record 22 with the medical data in the medical risk database 14 to identify whether medical data presented by the patient is associated with a risk of missed medical care opportunity. If so, information about additional medical care that would reduce the risk of a missed medical care opportunity is presented to the attending medical health care professional.

Examples of Associations in the Medical Risk Database

Examples 1–5 presented in tables at the end of this specification are examples of associations between patient data, increased medical risk and one or more proposed medical responses that can optionally be made by the medical risk database 14. Two examples of proposed medical responses are diagnostic steps, as shown in several of the examples, or treatment steps, shown for example in the Neck Pain table of Example 2.

The associations presented here are merely exemplary. A skilled health care professional who is familiar with the present disclosure and investigates medical liability results can readily find additional or alternative associations of the same type, useful for addressing the same or other medical conditions. Medical risk information is available from Daniel J. Sullivan, M. D., J. D., *High-Risk Acute Care: The Failure to Diagnose* (1998). This publication is incorporated by reference. A medical risk database incorporated in the PulseCheck® medical charting system is commercially available from IBEX Systems Group, Ltd. sometimes known as IBEX Healthdata Systems, 5600 N. River Road, Suite 150, Rosemont, Ill. 60018. The templates and medical risk data of the PulseCheck® medical charting system are incorporated by reference here. Other templates, medical risk data and medical charting systems can be used.

No representation is made that a health care professional should always follow the proposed advice, since it is not wise to rely solely on a preprogrammed database, unassisted by the judgment of a health care professional. The purpose of the medical risk database is simply to provide timely information to the health care professional that identifies and addresses a risk as it is presented.

Communication of Medical Risk

Figure 2:
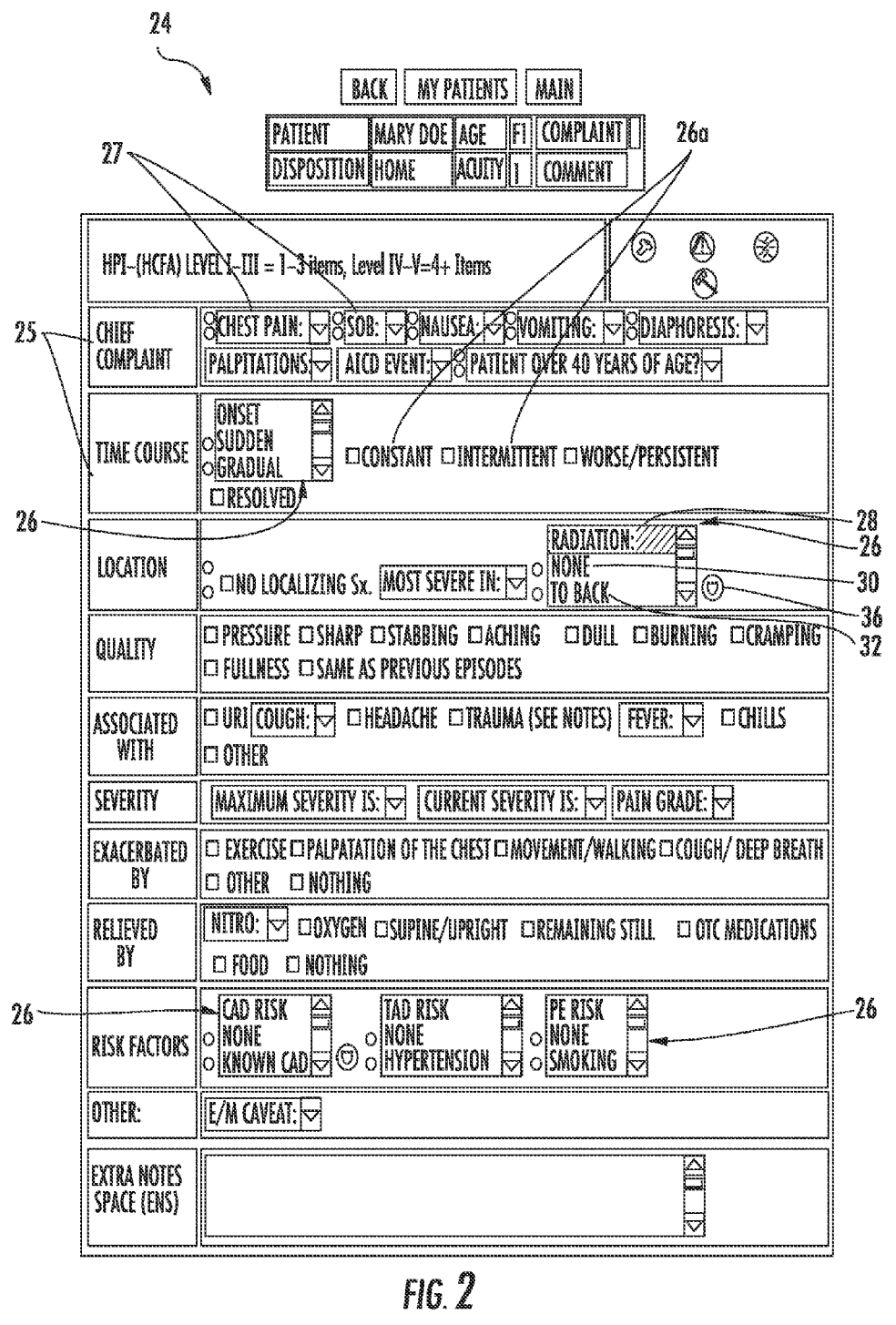

FIG. 2 shows a portion of an exemplary diagnostic template 24 that can be displayed on the communication device 18 when diagnosing a patient who complains of chest pain. This template 24, as with each template, includes a plurality of template sections. Each subsection 25 includes a plurality of queries 26, each relating to an observable patient medical condition (i.e.: whether the patient is vomiting, is nauseated, has chest pain). A query could be presented in the form of a checkable box (as with the query indicated as reference numeral 26a). Each query 26 includes a query heading 27 which identifies the patient medical condition for which the user is to input information. In the preferred embodiment, each query 26 includes a plurality of pre-selected observations (noted below) that the user can select. Each subsection also includes a plurality of qualifying statements, indicated generally as 26a, each having a checkable box. These qualifying statements can be selected by the user to narrow or further describe the information input by the user into the relevant query 26.

The template 24 as shown in FIG. 2 is in its initial condition, before a health care professional begins to respond to questions raised by the template or before the health care professional begins to input information into the queries 26. For example, the template 24 includes a query 26 to determine whether the chest pain is radiating toward the back. If not, "none" is marked by placing the cursor 28 on the "none" legend 30 for that answer and activating the choice (as by clicking a mouse button, if the cursor is moved by a mouse). The communication device 18 then displays that answer and the user is free to move on to other questions.

If the health care professional determines that the patient has chest pain radiating toward the back, "yes" is marked by placing the cursor 28 on the "to back" legend 32 for that answer and activating the choice. Other choices not shown in FIG. 2 are accessed by operating a scrolling button 34. Responsive to that answer, an icon 36 indicative of an increased medical risk is presented on the communication device 18.

Figure 3:
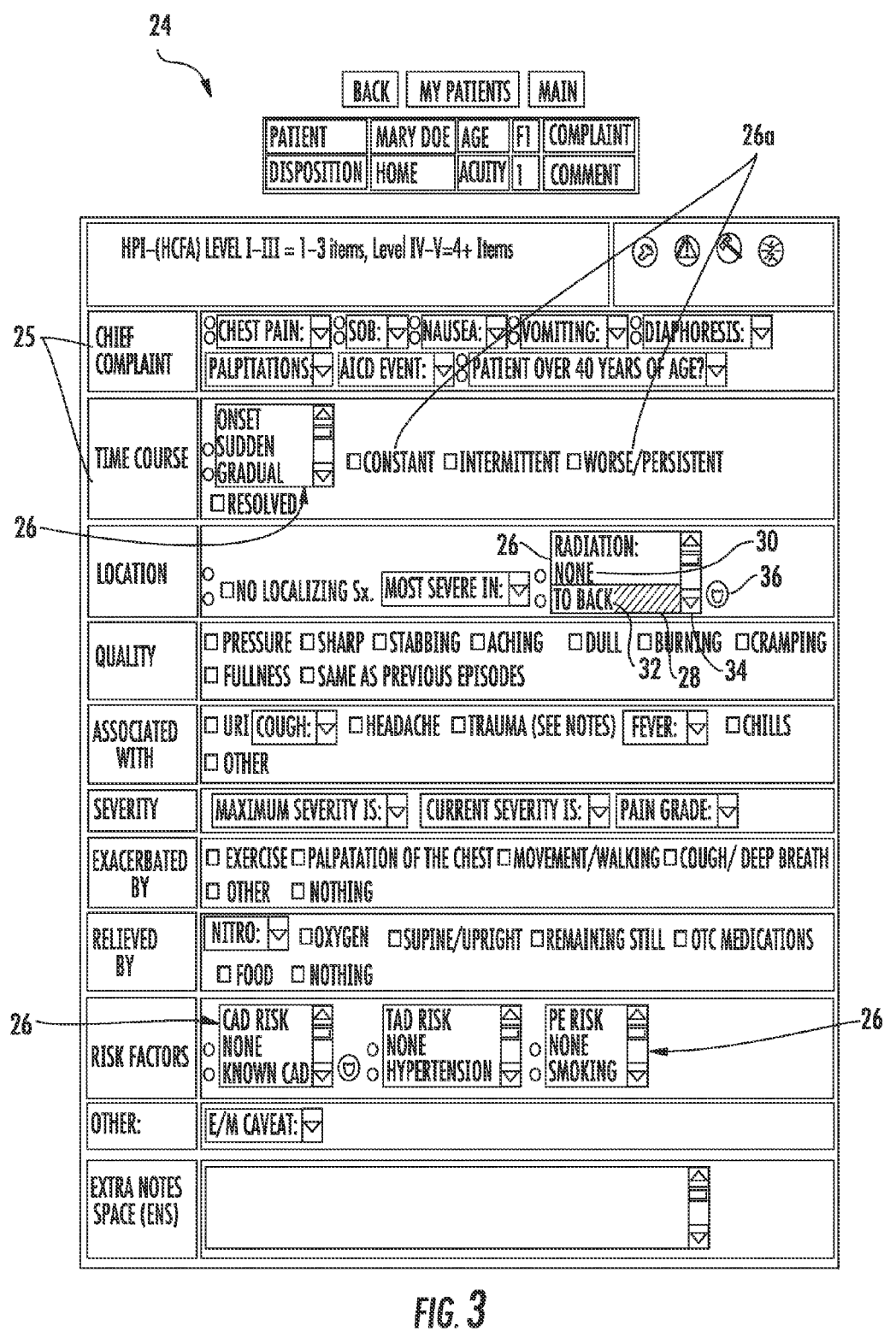

This icon 36 is displayed in FIG. 3, and is a fire-shaped, brightly colored icon that contrasts by its larger size and brighter red and orange colors with other indicia on the template 24. The icon 36 is also visible in FIG. 2, but is muted in color in FIG. 2 because it is not activated. The icon 36 is present in muted form before it is activated so a health care professional will not overlook the inquiry that activates the icon 36 when necessary.

Upon activation of the icon 36, the health care professional can click on or otherwise query the icon 36. This might be done to find out what medical risk is presented or what additional medical care is necessary to reduce the medical risk resulting when the chest pain presented by the patient is radiating toward the back. This query causes an additional care legend or message to be presented on the communication device 18, such as the pop-up legend 38 shown as FIG. 4: "Recommendation: Consider the diagnosis of Thoracic Aortic Dissection (TAD). Measure bilateral arm blood pressure, if possible. Look at the X-ray specifically for signs of TAD (e.g. abnormal aortic contour, widening of mediastinum, deviation of the trachea or mainstem bronchi). Document your observations." Thus, additional diagnostic steps are recommended to evaluate whether a TAD is present. The health care professional also is strongly encouraged to document his observations so the fact that the possibility of a TAD was thoroughly and quickly evaluated can be verified.

The medical risk raised by the symptom of chest pain radiating toward the back is that a TAD will be missed, as this is a condition that sometimes is not found quickly enough when a chest pain complaint is evaluated. This fact was ascertained by reviewing the scientific medical literature and the results of malpractice actions in which liability was found because a TAD allegedly should have been diagnosed soon enough to avoid further complications, but was not.

This medical risk has two components. One component is that a health care professional must recognize the possibility of a TAD very rapidly to reach the best possible patient outcome.

The other component is that, even if the health care professional quickly recognizes and properly evaluates the possibility of a TAD, but rules it out as inconsistent with other diagnostic indications, the pertinent facts must be documented in the patient's chart immediately. Even if the patient's condition has been properly evaluated as ruling out a TAD, an anomalous TAD could exist that would not have been recognized by even a skilled physician. Alternatively, the patient might not be suffering from a TAD initially, but may develop this condition shortly after the diagnosis that no TAD is present. If the symptoms presented by the patient at the time of diagnosis are properly and quickly evaluated and documented, the best possible care has been given, and the health care professional will be able to show this fact by reference to the patient's chart.

The present invention addresses the need to quickly evaluate and document TAD in a patient presenting chest pain that radiates to the back. The template 24 responds to the selection of this characterization of the chest pain immediately by presenting a distinctive and unusual warning, here the fire icon 36, that additional diagnostic work is necessary to rule out an increased medical risk of a TAD in this instance. This information is presented only when it is needed, so if this condition is not presented there is no need to alarm or distract the medical health professional by presenting this information.

The present invention works equally well to signal the need for additional care, whether diagnostic or therapeutic, when other conditions posing an increased medical risk are presented.

Red-Light Green-Light Prompting

Insurance company data and the scientific medical literature clearly indicate that poor medical record documentation, inadequate history taking and inadequate physical examinations are among the leading causes of medical errors, patient injuries and medical malpractice lawsuits. This part of the invention is designed to prompt health care practitioners to address factors in the history and physical examination that are critical to documenting a complete medical record, identifying important factors in the patient's history and physical examination, reduction in medical errors and resulting medical malpractice lawsuits.

The factors deemed critical to medical record documentation have been identified through an investigation by Daniel J. Sullivan, M.D., J.D., FACEP, into the scientific medical literature (multiple publications in the ED Legal Letter), and an analysis of over 100 malpractice lawsuits published in Dr. Sullivan's *High Risk Acute Care: The Failure to Diagnose*, noted herein above.

As noted above and as shown in FIGS. 2, 3, 5 and 6, each template 24 includes a plurality of queries 26. Each query 26 includes a red light prompt 52 and a green light prompt 54. The program displays or highlights the red light prompt 52 (as shown in FIG. 2) when the user has entered no input into the query 26. However, then the user inputs information into the query 26, the program displays or highlights the green light prompt 54. The prompts 52, 54 provide a visual display indicating to the user whether information has been observed or collected and input in the system 10. The red light prompts 54 and the green light prompts 52 form a red-light, green-light system. Other types of prompts are possible.

The red-light, green-light system are merely prompts, they are not mandatory. However, use of these prompts in a research setting, has led to an unprecedented level of documentation as demonstrated through the published, juried, scientific publication of Supplement to Annals of Emergency Medicine, October 2000 Volume 36 Number 4, Abstract # 110 entitled "On-Line Risk Management Combined With Template-Based Charting Improves the Documentation of Key Historical Data in Patients Presenting With Chest Pain".

In addition, the use of the electronic template format allows the application of medical logic. It is impossible to know what factors in the history and physical examination are essential in patient care without some initial input from the practitioner. Once the practitioner begins entering information, the system 10 responds by allowing previously invisible red-lights, green lights to become visible.

Figure 8:
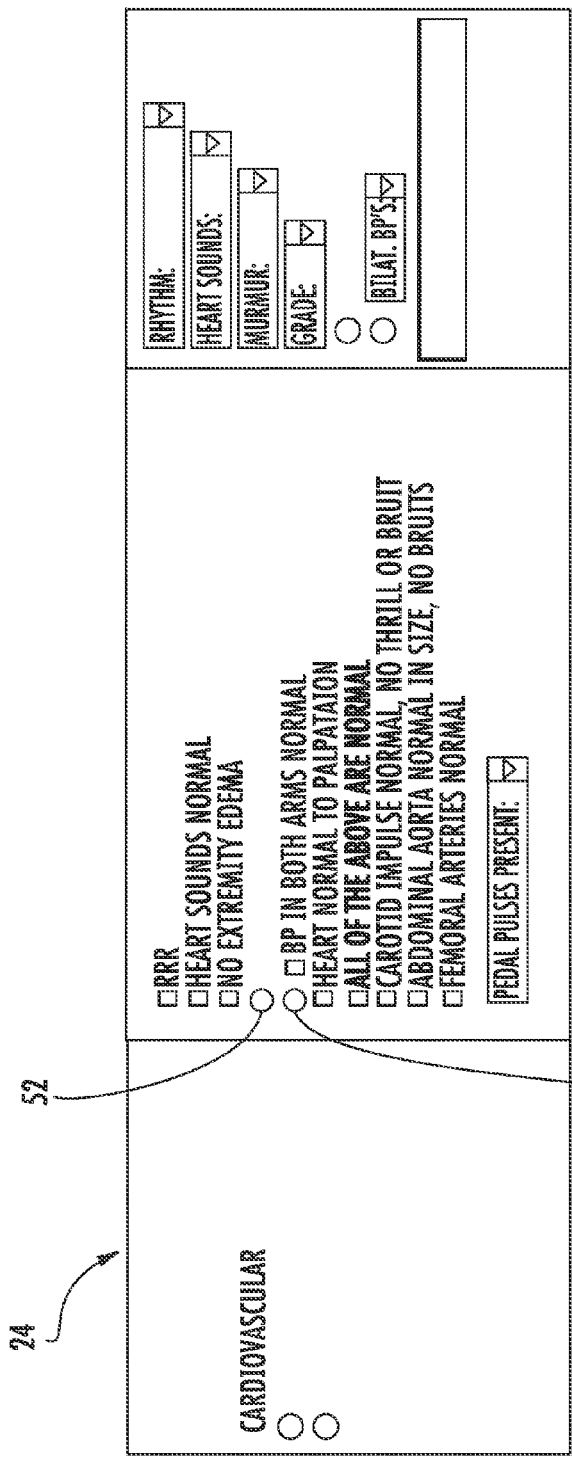
FIG. 8 is yet is another illustration of a screen display of the chest pain electronic medical record template showing the "cardiovascular" subsection.
Figure 9:
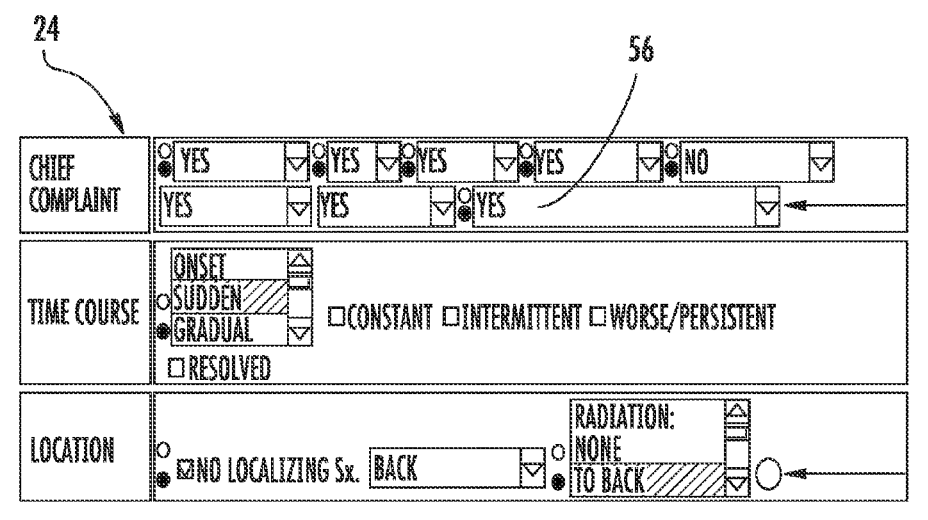
Figure 10:
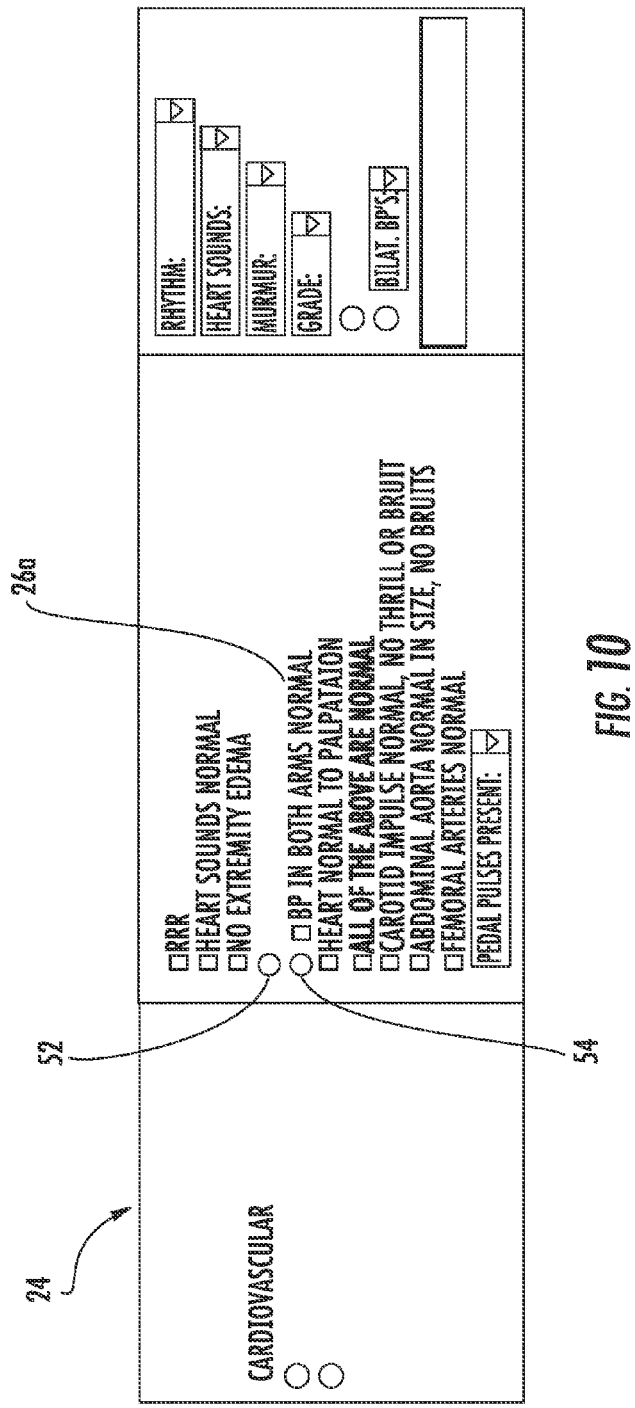
FIG. 10 is yet is another illustration of a screen display of the chest pain electronic medical record template showing the "cardiovascular" subsection.

FIG. 7 is an example of an uncompleted chest pain template 24. Note the field generally designated as reference number 56 which posses the following question to the medical care provider in the "complaint" subsection 25: "Patient over 40 years of age?" Patient's over 40 years of age complaining of chest pain often suffer from Thoracic Aortic Dissection, which can be detected by measuring the blood pressure in both of the patient's arms. FIG. 8 is an illustration of an uncompleted "cardiovascular" subsection 25. Note the lack of red-light, green-light prompts 52, 54 associated with the checkable box query 26a which states, "BP in both arms normal". FIG. 9 is an illustration of a chest pain template where the "complaint" subsection 25 has been completed. Note that the medical care provider has indicted that the patient is over 40 years of age in the field generally designated as reference number 56. In response thereto and as shown in FIG. 10, the system 10 has displayed a set of red-light, green-light prompts 52, 54 proximal to the checkable box query 26a which states, "BP in both arms normal". Thus, the practitioner measures the patient's bilateral blood pressures, documents the result, specifically looking for and documenting the examination for a Thoracic Aortic Dissection.

The red-light, green light prompts 52, 54 also assist the practitioner in considering the differential diagnosis. In the typical patient medical presentation, the patient first states a problem. Based upon this problem, or chief complaint, the practitioner then considers a list of possible diagnoses, called the differential diagnosis. This list of possible diagnoses guides the practitioner as to what questions to ask, what organ systems to evaluate, and which diagnostic tests to order. The prompts 52, 54 assist the practitioner in considering the diagnoses, which are prone to being missed, or a particularly high-risk to the patient (i.e.: family history of certain illnesses, hypertension, etc.). The differential diagnosis each have a drop down list of risk factors 62, allowing the physician a method for immediate recall of difficult to remember historical items.

Figure 12:
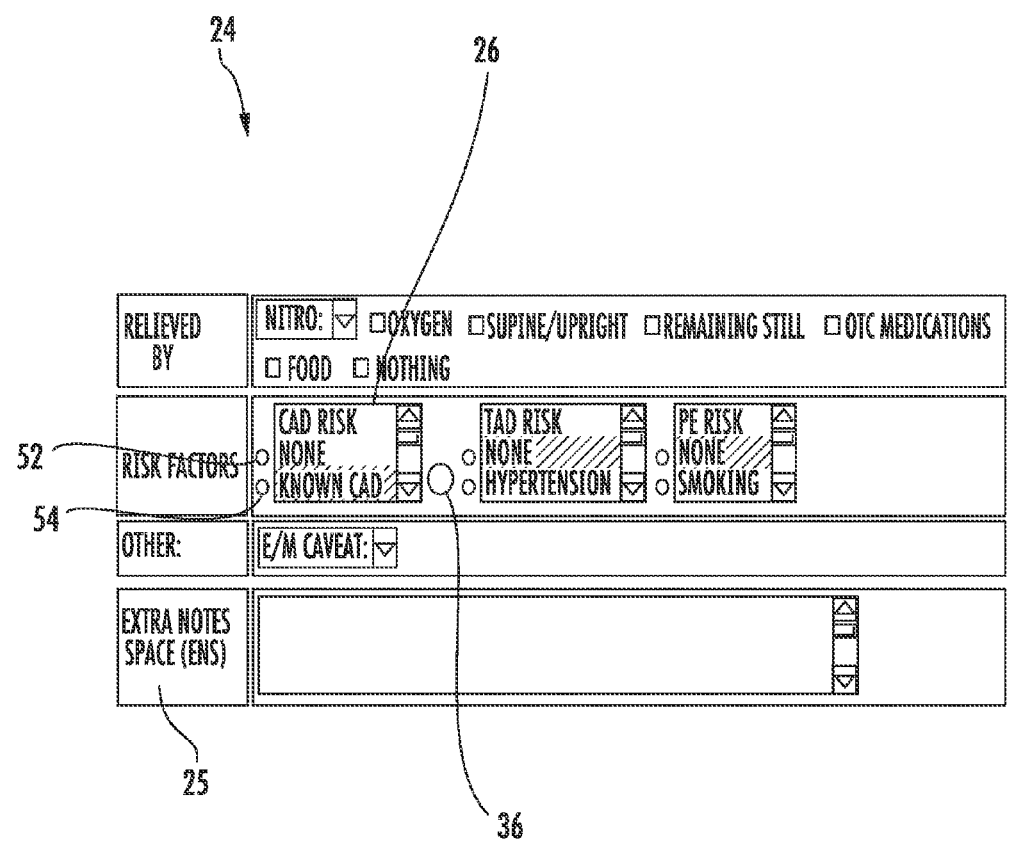

This function is demonstrated in FIGS. 11 and 12. FIG. 11 is an illustration of the risk factor section 25 of a template 24 as it would appear prior to entry of information in the queries 26. As shown in FIG. 12, upon selection of a risk factor in the first query, indicated as reference numeral 72, the system 10 highlights that query's green light prompt 54, and displays the fire icon 36 indicating to the user that a missed care opportunity may be present. Upon selection of the icon 36 by the user, a pop-up legend 38 (as illustrated in FIG. 4) appears indicating other observations, which should be performed by the health care provider. As noted above, the recommended observations are derived from prior occasions where a health care provider made an incorrect diagnosis because of the lack of additional observations by the health care provider.

Key Information Icons

Medical Practice is complex. Practitioners must remember or refer to a reference for a wide range of information. In actual practice, it is not possible to remember for an entire career, long lists of nerves with their specific function, long lists of tendons and how to test them, trauma scoring, croup scoring, Apgar scoring for the newborn, new standards of care and too many other lists, scores and other items to mention.

The simple fact is that practitioners need immediate reference to large amounts of diverse information that is often not immediately available in text, or on line. In addition, the busy practitioner seldom has time for looking up reference information.

As shown in FIG. 13, based upon research and practice, the program provides immediate access via key information icons 58 to lists of critical information, anatomical drawings, scores of various kinds, updates on standards of care, tendon identification and testing. This information may be stored within the system 10, or may be accessed via the Internet or a Local Access Network (LAN) or the like. Further, this information may be graphical or textual.

Figure 14:
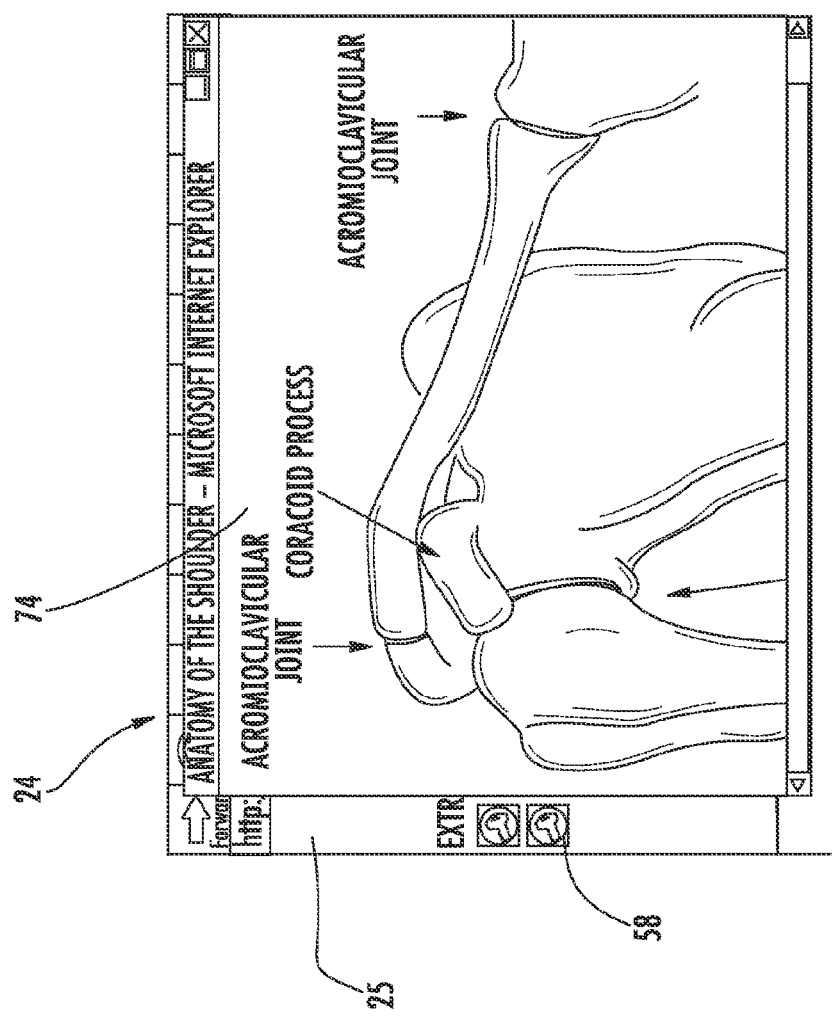
FIG. 14 is an illustration of an information icon screen display.

FIG. 13 is a screen display illustrating a subsection 25 of the shoulder injury. There are four key information icons 58 in the gray area labeled "extremity exam". The practitioner can place a cursor or touch mechanism over the labeled icons 58 and with a single click, the program will provide an information icon screen display 74 which demonstrates the anatomy of the shoulder (see FIG. 14). Thus, the practitioner has immediate access to information, which simply may not be available in many medical settings.

Immediate Identification of High Risk Diagnoses

When patients present to an emergency department with a medical problem, in most cases, they first see a nurse in an area outside of the department, called triage. Triage is the sorting of patients by severity of illness. There are several illnesses that are so acute, that intervention must be immediate or the patient may suffer severe injury. The group of diagnoses includes such things as the following: chest pain in a patient over 35 years of age; a patient presenting a cold pulse-less extremity; a child under 2 months of age with a fever, etc.

Figure 15:
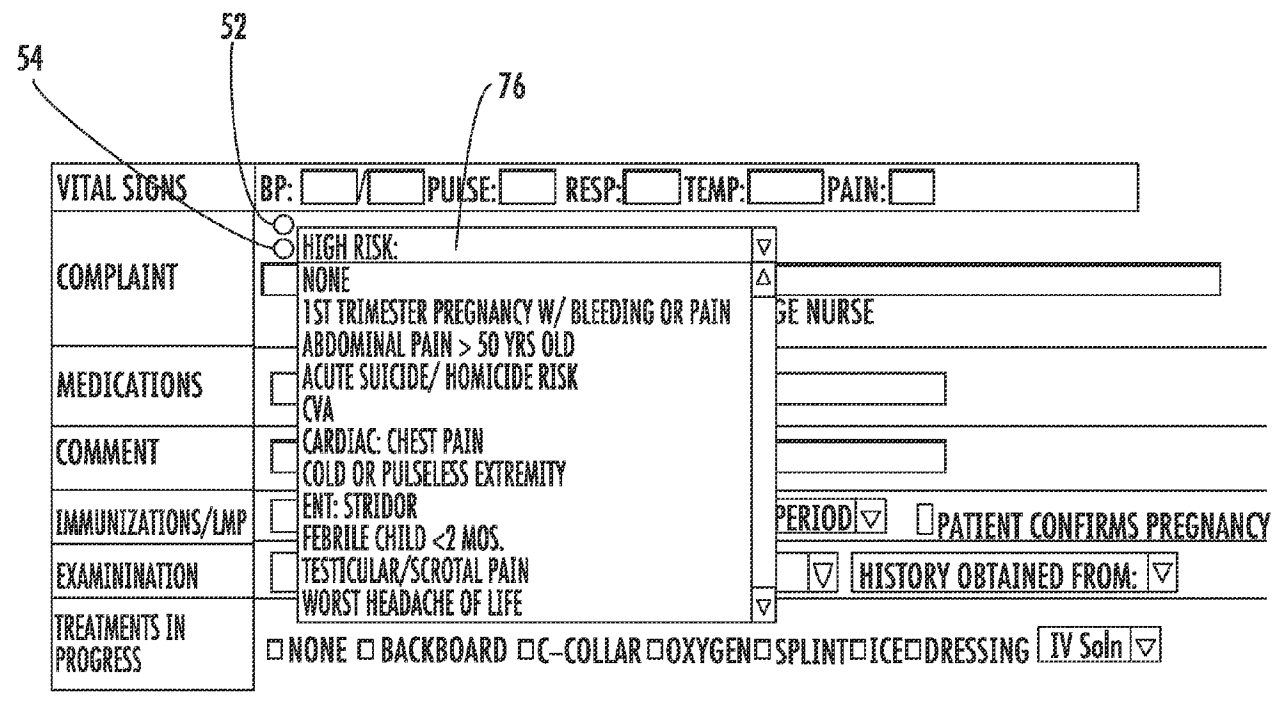

It is critical that the staff in triage recognize this small group of acute emergencies and communicates this to the appropriate individuals, such as the physician on duty in the emergency department or the charge nurse. As shown in FIG. 15, this invention provides the triage nurse with an electronic template, which includes a drop down list of these high-risk acute presentations 76. That part of the template contains a red-light, green-light prompt 52, 54, and in order to obtain a high level of compliance with the use of this function, the triage nurse must, at a minimum, select "none".

Figure 16:
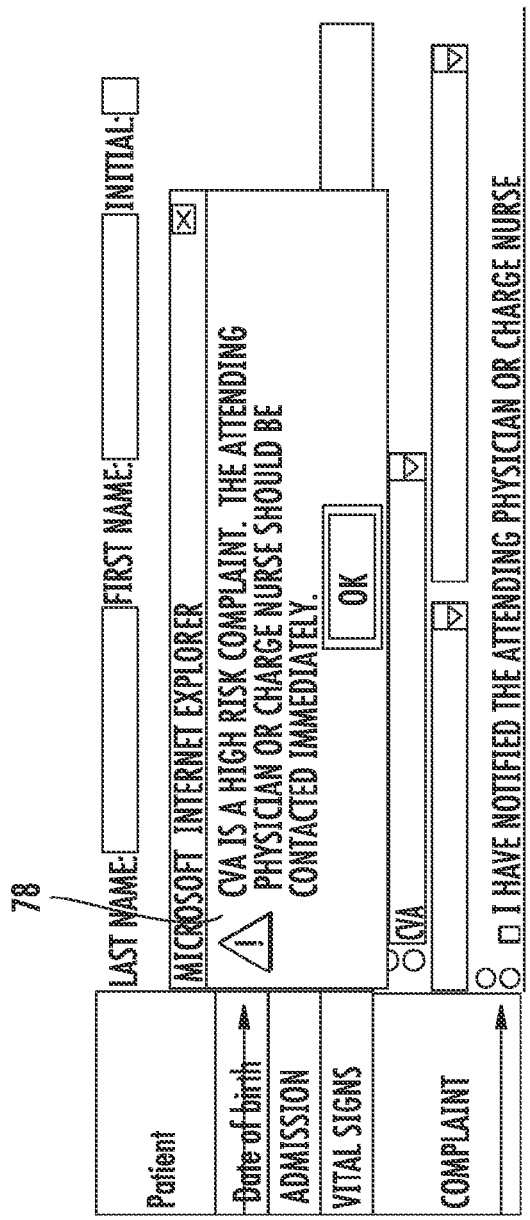
FIG. 16 is an illustration of a screen display of an electronic medical record template showing a visual warning to the triage nurse or other user to contact an attending physician or charge nurse.
Figure 17:
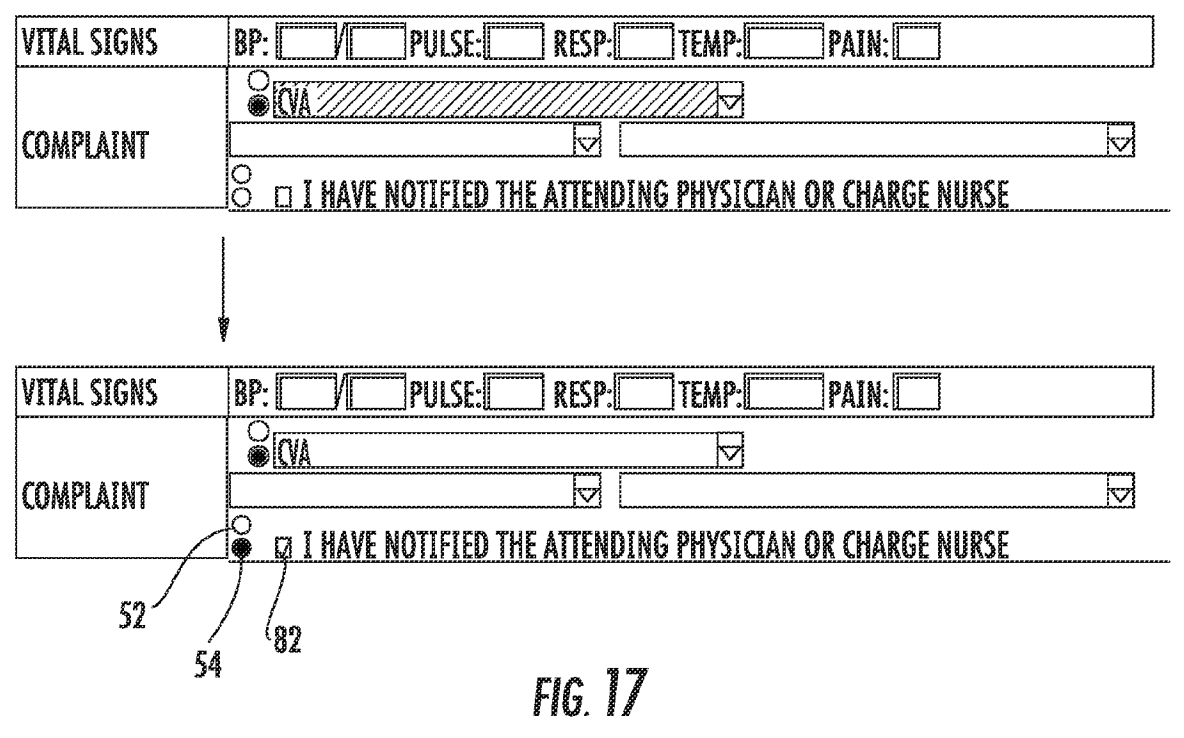

As shown in FIG. 16, if the nurse chooses one of these high-risk diagnoses, the program immediately pops up a warning 78 indicating that immediate notification of the physician or charge nurse must occur. Referring to FIG. 17, once the physician or charge nurse has been notified, then the triage nurse completes or "checks" a box 82 associated with a statement indicating that the physician or charge nurse has been notified. A red-light, green-light prompt 52, 54 associated with this statement then notes that this task has been completed. In this fashion, the combination of the red-light, green-light prompt 52, 54 and the high-risk list 76 assists the triage nurse in quickly identifying the acute emergencies, making the patient a high priority for treatment in the emergency department, and in recording the interactions between the triage nurse and the physician or charge nurse. Other types of prompts can be used.

Nursing Reevaluation of Patient Condition

Consistent and timely reevaluation of a patient's medical condition while the patient is in the waiting room, in the emergency department or the like, waiting for test results, a transfer or the like is critical to ensure discovery of changes in the patient's condition. An undetected change in a patient's medical condition increases the risk of a missed medical care opportunity. Therefore, to ensure consistent and timely reevaluation of a patient's medical condition, especially in chaotic environments such as a hospital emergency room and the like, the present system 10 includes a patient reevaluation template 84 which provides medical personnel with timed reminders of when to perform a reevaluation.

Figure 18:
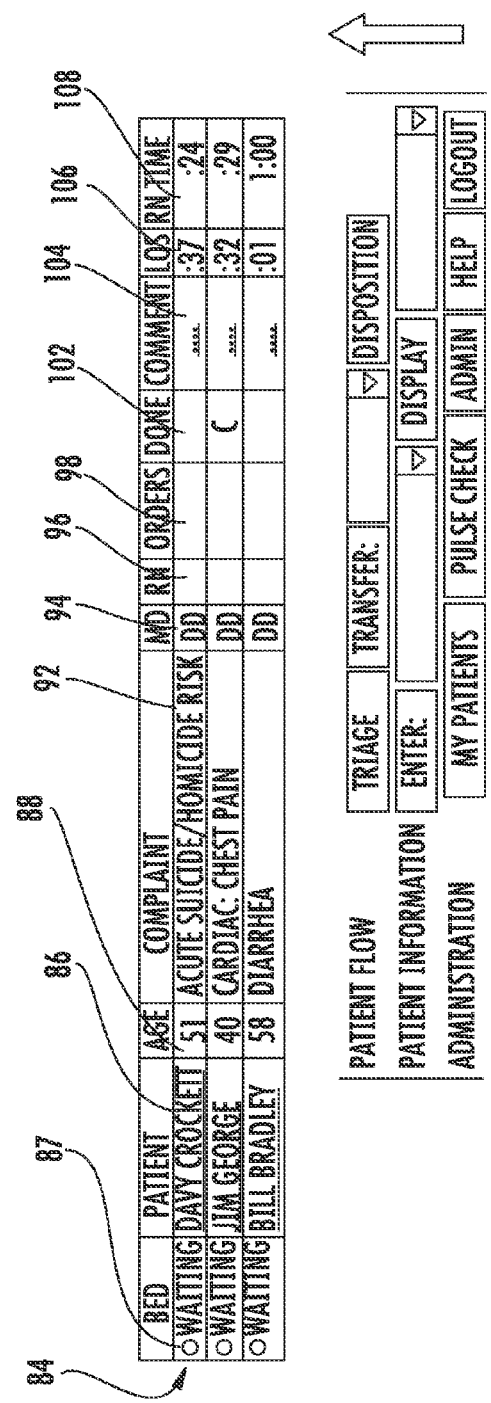
FIG. 18 is an illustration of a screen display of a patient reevaluation template.

Referring to FIG. 18, the patient reevaluation template 84 is provided having a "patient" name field 86 which, when selected, displays a list of templates 24 (not shown) created for the patient, a "bed" field 87 for indicating whether the patient is waiting for a bed or for indicating the bed or stretcher location, an "age" field 88 for displaying the patient's age, a "complaint" field 92 for displaying the patient's chief complaint, an "MD" field 94 for displaying the initials of the patient's treating physician, an "RN" field 96 for displaying the initials of the nurse charged with the patient's care, an "order" field 98 for a listing of any pending orders ordered by the treating physician (i.e. lab tests, CAT scans and the like), a "done" field 102 which provides the nurse or physician a visual indicator of the status of a patient (i.e. the "done" field displays a "C" after a chart template has been completed for a patient, an "X" after a patient has been X-rayed, and displays a green color when all treatment has been completed), a "comment" field 104 for listing and/or entering general information about the patient, a length-of-stay or "LOS" field 106 for indicating the length of time for which the patient has been present in a particular department (i.e. the emergency room), and an "RN time" indicator 108. The RN time indicator 108 counts down from a pre-set specified time period. In one embodiment, the RN time indicator 108 provides a visual and/or audible warning that a predetermined amount of time remains before reevaluation is due. For example, the RN time indicator 108 may change colors so that the field turns yellow when 25% of the total time remains, and turns red when 10% of the time remains.

With the knowledge provided by the RN time indicator 108, the RN reevaluates the patient before time elapses, consistent with department policy and good patient care. Any documented reevaluation (i.e. by obtaining vital signs or entering an assessment note) resets the RN time indicator 108 to the specified time period.

In the preferred embodiment, if the health care provider fails to reevaluate the patient within the specified time period, the RN time indicator 108 provides a visual and/or audible warning that reevaluation is required. Further, the RN time indicator 108 counts forward from the expired time period to give an indication how far the health care provider has allowed the reevaluation period to extend. For example, in the template 84 illustrated in FIG. 19, the RN time indicator indicated by reference number 109 for the patient named "Davy Crockett" indicates that the pre-set time period has expired, and that reevaluation is one minute overdue.

The system 10 records all patient reevaluations. Specifically, the system 10 records each time the RN time indicator 108 is reset, the time period between each reevaluations, and who performed the reevaluation. The system 10 then later generates a report based on this recorded information that can later be used for assessments, teaching, litigation, etc. For example, the report can be used to access whether a nurse or physician is consistently performing reevaluations beyond the allotted time period.

Vital Sign Alerts

A patient's "vital signs" provide an indication of a patient's medical condition. A patient's vital sign is considered "normal" when it falls within a standardized "normal range". A normal range is a predetermined range of numerical values within which a patient's vital sign should statistically fall in the absence of a medical ailment. Vital sign normal ranges are known by those skilled in the medical arts, and are widely published. The maximum and minimum values for these normal ranges vary depending on the patient's age. However, numerous measurable vital signs exist and for each vital sign there exists numerous possible normal ranges. Therefore, is it critical that the medical care provider recognize when a patient's vital sign or signs fall outside the corresponding normal range. Failures to recognize that a vital sign falls outside the corresponding normal range may result in an increased risk of a missed medical care opportunity. Often, such missed medical care opportunities occur when a patient is being discharged from a hospital or the like, and the discharging nurse or physician fail to recognize that the patient's vital signs are abnormal.

Figure 20:
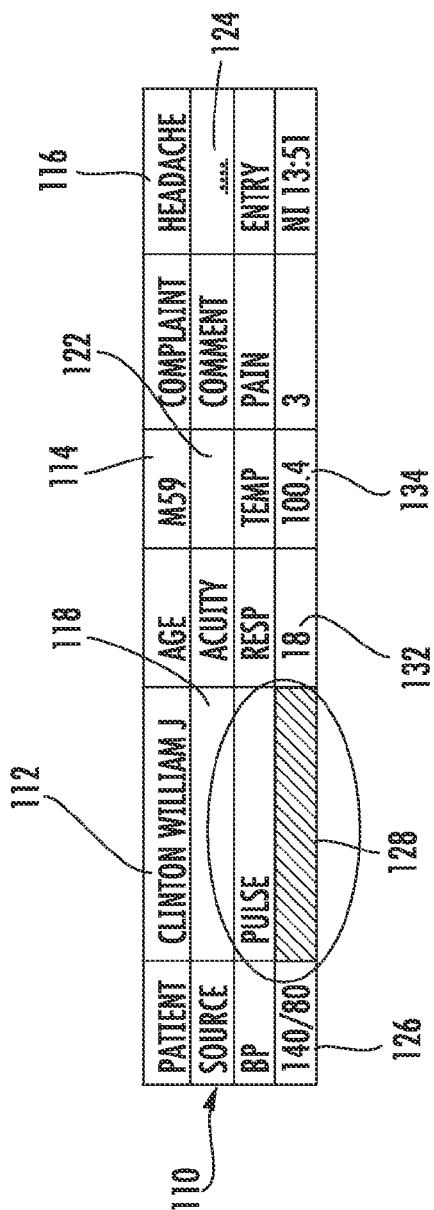
FIG. 20 is an illustration of a screen display of a vital sign template.

A patient's vital signs may be collected manually by a nurse, physician or other health care provider, or may be collected using commercially available apparatuses capable of collected information such as a patient's blood pressure, pulse, blood-oxygen content, temperature and the like. As shown in FIG. 20, this collected information is displayed on a vital sign template 110. The patient's vital signs are visible when looking at the screen. A warning is provided automatically when the vital signs are severely abnormal or above normal.

In the preferred embodiment, the vital sign template 110 includes a "patient" field 112 for displaying the patient's name, an "age" field 114 for displaying the patient's age, a "complaint" field 116 for displaying the patient's chief complaint, a "source" field 118 for displaying the source or location of the patient's chief complaint, an "acuity" field 122 for displaying the acuity level of the complaint, and a "comment" field 124 for imputing and/or displaying comments regarding the patient. Fields for displaying the patient's blood pressure 126 (labeled "BP"), pulse 128 (labeled "pulse"), respiratory rate 132 (labeled "resp") and temperature 134 (labeled "temp") are provided. This information can be automatically imported from the above-noted commercially available vital sign collection apparatuses, inputted manually directly into the template 110, and/or imported from another template.

The numerical values for each of the patient's vital signs are compared against normal ranges stored in the medical risk database 14. Where a vital sign falls outside the normal range for a typical patient, the medical care provider is alerted visually and/or audibly that the particular vital sign falls outside the corresponding normal range. By alerting the medical care provider as such, they can then intervene to determine whether medical attention is required, thus substantially reducing the risk of a missed medical care opportunity.

FIG. 21 is an example of a completed vital sign template 110 as viewed by a discharge nurse or physician as a patient is being discharged. In this example, the patient's pulse as displayed in the pulse field 128 has a value of "140". The pulse normal range stored in the medical risk database 14 for a statistically similar patient is 50 to 100. In this case, the patient's pulse falls outside the corresponding normal range. To visually alert the discharge nurse or physician of this fact, the pulse field 128 is highlighted, preferably in red. By alerting the discharge nurse or physician of this abnormal vital statistic, the risk of overlooking this abnormal value is substantially reduced, thus substantially reducing the risk of a missed medical care opportunity.

As a rather warning or alert to the discharge nurse or physician, when a "discharge" button (not shown) is selected by the discharge nurse or physician (thereby indicating that the patient is being discharged), a visual statement appears on the communication device 18 indicating the exact abnormal vital sign, and displays the normal range for that vital sign. To continue with the patient discharge, even in light of this warning, the discharge nurse or physician must select a "continue" button 135. The system 10 then records the fact that a warning was provided to the discharge nurse or physician, and that the discharge nurse or physician selected the "continue" button 135 despite the information contained in the warning. The system 10 then later generates a report based on this recorded information that can later be used for assessments, teaching, litigation, etc. regarding what actions were specifically taken by the discharge nurse or physician, and whether such actions were proper or improper.

Report Generator

All information input into the system by all users is recorded by the system 10, and this information is later collated to generate a printed report. For example, after the user has finished completing all of the relevant templates 24, 84, 110, the system 10 generates a report indicating the information contained therein, even if such information indicates that no observations were present or observable for a particular condition. This report can later be used for assessments, teaching, litigation, etc. regarding what actions were specifically taken by the user, and whether certain observations were made.

Allergy and Drug Interaction Alerts

Alerting medical personnel (i.e. physicians, nurses, pharmacists and the like) that a patient has a particular allergy substantially reduces the risk of missed medical care opportunities. Computer software currently exists which can be utilized to notify medical personnel who are responsible for a given patient's care of that patient's allergy. In addition, such software can alert a medical care provider when a given course of treatment is likely to trigger an allergic reaction. Such software is widely commercially available, and one with ordinary skill in the art could select the appropriate allergy and drug interaction software for their needs and implement the software in conjunction with the present invention. Typically the patient allergy is conveyed from the patient to a medical care provider during triage and manually inputted, automatically imported from an independent database, or where such software is used in conjunction with the present invention, that this information is contained in a preexisting patient data record 22 already stored within the system 10.

FIG. 22 is a screen illustration of a prescription medicine template 136 provided by an allergy and drug interaction software program. The prescription medicine template 136 displays for a medical care provider a list of all medications currently prescribed for a patient, and is a means by which the medical care provider can add and remove prescription medications to and from the list. The template 136 includes a patient "known allergy" field 138 that displays all known allergies associated with the patient. A "prescription" field 142 displays the name, form (i.e. liquid, tablet, and the like), dosage, and delivery form (i.e. oral, intravenous and the like) of the medication. A "dispense" field 144 lists the number of times the prescription is to be filled. A "quantity" field 146 lists the numerical value for the amount of medication to dispense, and a corresponding "unit" field 148 lists the units of measurement (i.e. milliliters, "cc's" or cubic centimeters or the like) for the numerical "quantity" field 146 value. A "schedule" field 152 lists the time or frequency the medication is to be administered to the patient. "Remove" and "write" check fields 154, 156 allow a medical care provider to remove a prescription from the list of medications to be administered, and to add a prescription to the list of medications to be administered, respectively.

In the example provided in FIG. 22, the medical care provider added penicillin to the list of medications to be administered to the patient. However, as can be seen in the patient "known allergy" field 138, this particular patient is allergic to penicillin. When the medical care provider added penicillin to the list of medications to be administered to the patient, the entry was compared against the patient data record, and a conflict was recognized by the system. Once the conflict was recognized, the software then prevented prescription from being added to the list of medications to be administered to the patient. In the preferred embodiment, not only is the medical care provider prevented from adding the possibly allergic reaction inducing medication to the list of medications to be administered to the patient, but also an audible and/or visual alert notifies the medical care provider of this conflict and the medical care provider is provided with possible alternatives to the possibly allergic reaction inducing medication. In this example, the software visually alerted the medical care provider as to the conflict by highlighting the prescription field generally indicated by reference number 143 and color altering the field 143 to make it substantially more noticeable, and alternative medications were listed.

Not only does the software compare all newly entered prescriptions against patient allergy information contained in the patient data record 24, but the software also compares the prescription against information contained in the medical risk database 14 to determine if a "drug interaction" exists between the newly entered prescription medication and prescription medication already being administered to the patient. A "drug interaction" occurs when two or more medications are administered to the patient, and those medications interact with each other to produce undesired side effects. If a "drug interaction" exists, an audible and/or visual alert notifies the medical care provider of this "drug interaction" and notifies the medical care provider which drugs may cause the "drug interaction".

Figure 23:
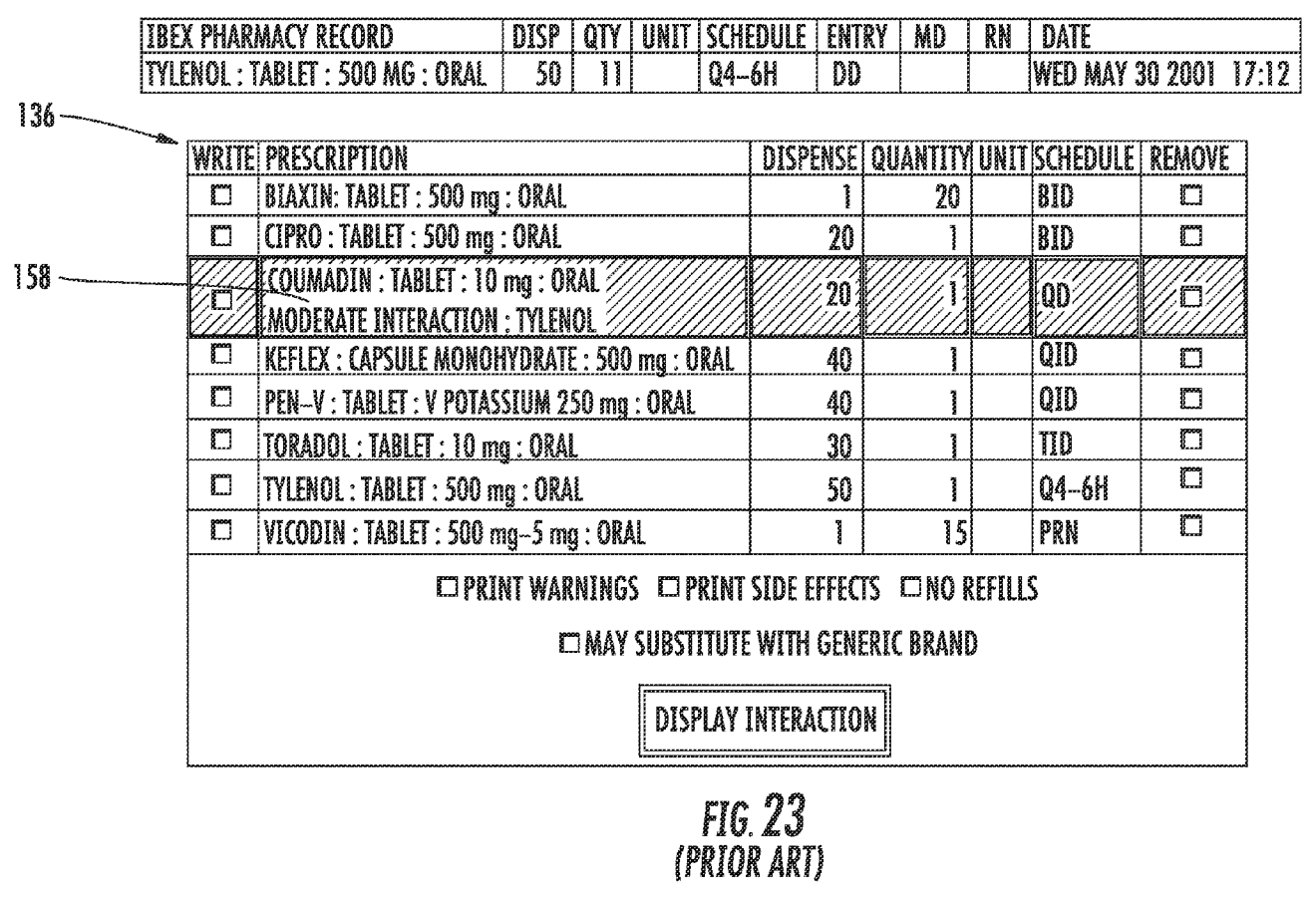

FIG. 23 is an illustration of an example of a prescription medicine template 136 where a "drug interaction" has been detected. In this case, when the medical care provider added the drug Coumadin to the list of medications to be administered to the patient, the entry was compared against the other medications already listed and against information contained in the medical risk database 14, and a "drug interaction" was recognized by the software. Once the "drug interaction" was recognized, the system 10 visually alerted the medical care provider as to the "drug interaction" by highlighting the corresponding prescription field (indicated by reference number 158) and color altering the field 158 to make it substantially more noticeable. Also, the name of the drug with which Coumadin is likely to interact with is also listed, namely, Tylenol. By using the allergy and drug interaction software program in conjunction with the present invention, medical personnel are alerted (i.e. physicians, nurses, pharmacists and the like) of potential "drug interactions," thus substantially reducing the risk of missed medical care opportunities.

EXAMPLE 1

Abdominal Pain

| Patient Data | Medical Risk | Proposed Response |
| --- | --- | --- |
| the patient is pregnant | A pregnant patient suffering from abdominal pain may have an ectopic pregnancy, which is not necessarily | Perform an ultrasound study of the fetus and surrounding maternal tissue. |

-continued

| Patient Data | Medical Risk | Proposed Response |
| --- | --- | --- |
| | determinable by physical examination and may be misdiagnosed as another condition. | |
| woman of child bearing age with abdominal pain | Patients reporting information inconsistent with pregnancy, such as abstinence from intercourse, recent menstruation, or the use of contraceptives often are nonetheless pregnant. When a pregnant person presents abdominal pain, the diagnosis of ectopic pregnancy should be considered. | Test for pregnancy |
| sudden onset of abdominal pain | A vascular event that requires quick treatment, such as abdominal aortic aneurysm (AAA), may have occurred. AAA is often overlooked, as it can be difficult to diagnose. | Test for a vascular event |
| The patient's abdominal pain radiates to the back or to the flank. | An AAA, which requires quick treatment, may have occurred. | Test for AAA |

EXAMPLE 2

Neck Pain

| Patient Data | Medical Risk | Proposed Response |
| --- | --- | --- |
| Blunt spine injury less than eight hours before the time of diagnosis. | In a number of cases, liability has been found because the patient was diagnosed with a spinal cord injury several hours (but fewer than eight hours) after the injury, but methylprednisolone treatment to reverse the effects of spinal cord injury was not started early enough to improve the patient outcome. | Blunt spine injury is treated with high dose methylprednisolone if treatment is begun within eight hours of the injury. The literature does not demonstrate any benefit beyond eight hours. 30 mg/kg bolus administered IV over 15 min. 45 min. pause Maintenance infusion 5.4 mg/kg/hr for 23 hours |
| The patient is intoxicated with alcohol or other intoxicants. | The intoxication may mask the effects of cervical spinal cord injury or render the patient unable or unwilling to cooperate. | Liberal ordering of the trauma C-Spine series is recommended in this setting. |
| Neck pain, but no radiologic (i.e. bone) abnormality in the x-ray and no apparent neurological changes. | Spinal cord injuries do not always coincide with spine damage visible on x-rays or stable neurological changes. Transient neurologic changes may occur before the emergency department visit, and not be present in the emergency | Don't rely solely on the absence of radiological abnormality and of present neurological symptoms. Look carefully at EMT (emergency medical technician) and nursing notes relating back to the time of the injury. |

-continued

| Patient Data | Medical Risk | Proposed Response |
|---|---|---|
| | department. Spinal Cord Injury Without Radiological Abnormality (SCIWORA) is often very difficult to diagnose, sometimes with catastrophic results. | If there is prior evidence of a neurologic sign or symptom, neurosurgical consultation, a period of observation or hospital admission are recommended. |

EXAMPLE 3

Chest Pain

| Patient Data | Medical Risk | Proposed Response |
|---|---|---|
| Chest Pain Radiating to the Back | This is a characteristic symptom of Thoracic Aortic Dissection (TAD), which is often missed in diagnosis because it often resembles other, less-critical conditions. TAD must be quickly diagnosed and treated to avoid death. | Consider the diagnosis of TAD. Measure bilateral arm blood pressure, if possible. Look at the x-ray specifically for signs of TAD (e.g. abnormal aortic contour, widening or mediastinum, deviation of the trachea or mainstem bronchi). Document your observations. |
| Chest pain PLUS: One major risk factor (smoking, hypertension, diabetes, family history (HX), high cholesterol) or A history of coronary artery disease | Where chest pain is the only clinically apparent symptom of an acute myocardial infarction (AMI), that diagnosis is often prematurely ruled out in favor of other possible conditions (often due to coinciding symptoms of lesser problems, like indigestion) and the patient is discharged. This delayed or missed diagnosis frequently results in death of the patient. | Do one of the following: Obtain cardiology consultation Observation status to rule out myocardial infarction Admit |

EXAMPLE 4

Headache

| Patient Data | Medical Risk | Proposed Response |
|---|---|---|
| This is reported as the worst headache of the patient's entire life. | This is a two-step risk. First, a very bad headache may be caused by a subarachnoid hemorrhage. Even though few severe headaches are caused by a subarachnoid hemorrhage, the patient outcome is poor unless the condition is quickly diagnosed and treated. | (1) Order a non-infused CT of the head to rule out a subarachnoid hemorrhage. (2) Proceed with lumbar puncture even if the CT of the head is read as negative for bleeding. |

-continued

| Patient Data | Medical Risk | Proposed Response |
|---|---|---|
| | Second, even if a 4$^{th}$ generation CT of the head is carried out, sometimes it will not be read as showing bleeding when the patient in fact has a subarachnoid hemorrhage. | |

EXAMPLE 5

Testicular Pain

| Patient Data | Medical Risk | Proposed Response |
|---|---|---|
| Abdominal pain, but no testicular pain | Torsion of the testicle is a difficult diagnosis, and is often missed, as often the patient's site of discomfort is in the abdomen, rather than the testicles. | Consider torsion in the differential diagnosis. |
| sudden onset of pain | Sudden onset of severe pain should rule out epididymitis, but often does not. Torsion testicle must be immediately diagnosed, since salvage of the testicle is only highly probable within six hours of the onset of pain. | Immediately consider the diagnosis of torsion testicle |

The foregoing description of an embodiment of the invention has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and various modifications as are suited to the particular use contemplated. It is intended that the scope of the invention not be limited by the specification, but be defined by the claims as set forth below.

What is claimed is:

1. A computerized medical chart system for improving the medical care of patients by communicating with a health care professional preparing a medical record in connection with preparing or recording diagnoses, symptoms, treatment or other patient information, and including important elements of the patient's medical condition, comprising:
a medical risk database containing medical care information regarding a plurality of illnesses, diseases and/or injuries, and further at least containing information regarding increased risks of missed diagnoses;
means for prompting the health care professional to record symptoms, or other patient information relevant to the increased risks;
means for comparing the recorded symptoms or other patient information with, the medical care information stored in the medical risk database to determine the existence of at least one increased risk of a missed diagnosis based on the symptoms recorded;
means for associating said recorded symptoms or other patient information with the relevant medical care information related to the increased risk of missed diagnoses with respect to the recorded symptoms or patient information;

means for providing medical care information to the health care professional so as to reduce the risk of the health care professional missing at least one diagnosis from the plurality of illnesses, diseases or injuries based on the symptoms or other patient information regarding the patient;

means for automatically prompting the health care professional to take particular actions or record additional important items of said diagnosis, symptoms, treatment or other patient information in said medical record, in an interactive fashiom so as to provide the health care professional with an opportunity to avoid a missed diagnosis and to adequately record the action taken; and means for alerting the health care professional to consider one or more medical conditions leading toward possible diagnoses based upon input of information correlating with said increased risk information in said database.

2. The invention according to claim 1 wherein said system further includes at least one key information icon associatedi with said medical record so as to provide immediate access to said medical care information to said health care professional.

3. The invention according to claim 1 wherein said system further includes an interactive diagnostic template for one or more symptoms leading to a medical diagnosis.

4. The invention according to claim 3 wherein said interactive diagnostic template the said symptoms leading to a diagnosis is capable of providing access to additional medical care information relating to said symptoms.

5. The invention according to claim 3 wherein said interactive diagnostic template for said symptoms leading to a dagnosis further includes a presentation of relevant acute life threatening situations.

6. The invention according to claim 1 wherein said system further includes means to document an acute emergency.

7. The invention according to claim 6 wherein said means to document an acute emergency comprise an alarm response and a vital signs alert.

8. The invention according to claim 1 wherein said system further comprises means for indicating a high-risk diagnosis.

9. The invention according to claim 1 wherein said system further comprises means for mandatory notification to the healthcare professional.

10. The invention according to claim 1 wherein said system further includes timer means for setting a time limit for interaction with a patient.

11. The invention according to claim 1 wherein said system further comprises meas for warning the healthcare professional of abnormal patient vital signs.

12. The system of claim 1 wherein the information contained in the database comprises factors that should be addressed in connection with the diagnosis and treatment of the patients to ensure that the healthcare professional meets the requisite standard of care, and the means for prompting the healthcare professional comprises means to ensure that the healthcare professional has satisfied and documented that the necessary standard of care was met in treating the patient.

13. The computerized medical chart system of claim 1 wherein said medical risk database further includes information concerning reducing the risk of at least one of the following: incorrect or delayed diagnosis; or missed, incorrect or delayed treatment.

14. The computerized medical chart system of claim 1 further comprising warning means notifying the health care professional whether important information with respect to at least one sign, symptom, physical exam or other patient information leading to a diagnosis or treatment of the patient has been documented.

15. The computerized medical chart system of claim 14 wherein said warning means comprises at least one indicator signifying to the health care professional that the important information has been documented with respect to the medical condition of the patient.

16. The computerized medical chart system of claim 15 wherein said warning means comprises at least one light signifying to the health care professional that the important information has been documented with respect to medical condition of the patient.

17. The computerized medical chart system of claim 15 wherein said warning means comprises at least one light signifying to the health care professional that the important information has not been fully documented with respect to the medical condition of the patient.

18. A method for improving the medical care of patients by using a computerized medical chart creation system for communicating with a health care professional preparing a medical record in connection with recording diagnosis, symptoms, treatment or other patient information, and including important elements of the patient's medical condition, the computerized medical chart creation system including a medical risk database having information on a plurality of illnesses, diseases and/or injuries, the method comprising the steps of:

recording said symptoms or other patient information;

comparing said recorded symptoms or other patient information with the information stored in the medical risk database containing at least information regarding the risk of missed diagnoses as to the existence of at least one such increased risk with respect to the symptoms or other patient information;

presenting medical care information to said health care professional reducing the risk of a missed diagnosis as to the symptoms or other patient information regarding said plurality of illnesses, diseases or injuries; and prompting the health care professional to take particular actions and include important items of said diagnoses, symptoms, treatment or other patient information in said medical record, in an interactive fashion; and alerting the health care professional to consider one or more medical conditions leading toward possible diagnoses based upon input of information correlating with said increased risk information in said database.

19. The method according to claim 18 wherein said invention further includes at least one key information icon associated with said medical record so as to provide immediate access to said medical care information to said health care professional.

20. The method according to claim 19 wherein said system further includes an interactive diagnostic template for medical diagnosis.

21. The method according to claim 20 wherein said interactive diagnostic template for symptoms being diagnosed, is capable of providing access to additional medical care information relating to said symptoms.

22. The method according to claim 20 wherein said interactive diagnostic template for symptoms being diagnosed further includes a presentation of relevant acute life threatening situations.

23. The method according to claim 18 wherein said invention further includes the step of documenting an acute emergency.

24. The method according to claim 19 wherein said invention further comprises an alarm response and a vital signs alert.

25. The method of claim 18 wherein the information contained in the database comprises factors that should be addressed in connection with the diagnosis and treatment of the patients to ensure that the healthcare professional meets the requisite standard of care, and the step of prompting the healthcare professional comprises means to ensure that the healthcare professional has satisfied and documented that the necessary standard of care was met in treating the patient.

26. The method of claim 18 wherein said medical risk database further includes information concerning the risk of at least one of the following incorrect or delayed diagnosis; or missed, incorrect or delayed treatment.

27. The method of claim 18 further comprising the step of warning the health care professional as to whether important information with respect to at least one sign, symptom, physical examination or other patient information leading to a diagnosis or treatment of the patient has been documented by using warning means.

28. The method of claim 18 wherein said warning means comprises at least one indicator signifying to the health care professional that the important information has been documented with respect to the medical condition of the patient.

29. The method of claim 18 wherein said warning means comprises at least one light signifying to the health care professional that the important information has been documented with respect to the medical condition of the patient.

30. The method of claim 18 wherein said warning means comprises at least one light signifying to the health care professional that the important factors have not been fully documented with respect to the medical condition of the patient.

31. A computerized risk management system for assisting a health care professional in diagnosing, treating, and documenting actions taken with respect to possible illnesses, diseases or injuries of a patient, associated with a computerized medical chart preparation system comprising:
  a medical risk database containing information regarding a plurality of illnesses, diseases and/or injuries, and comprising medical care information regarding at least increased risks of missed diagnoses;
  means for prompting the health care professional to record symptoms or other patient information relevant to the increased risks of missed diagnoses;
  means to input data concerning the patient into a patient data record;
  a data processor, wherein the data processor compares the patient data in the patient data record with the medical care information in the medical risk database to determine the existence of an increased risk of at least one missed diagnosis of the patient having one or more of die illnesses, diseases or injuries;
  means to provide the health care professional with relevant medical care information concerning the possible illnesses, diseases or injuries to reduce the possibility of the healthcare professional missing at least one diagnosis regarding the illnesses, diseases or injuries; and
  means for further automatically prompting the health care professional to take appropriate action and record relevant patient information and the actions taken by the health care professional with respect to the patient in the medical record, in interactive fashion, so as to provide the health care professional with an opportunity to avoid at least one missed diagnosis, and adequately document the diagnosis of the illnesses, diseases or injuries and the actions taken; and
  means for alerting the health care professional to consider one or more medical conditions leading toward possible diagnoses based upon input of information correlating with said increased risk information in said database.

32. The computerized risk management system of claim 31 wherein said system further comprises warning means notifying the health care professional whether important factors with respect to the diagnosis or treatment of the patient have been appropriately documented.

33. The computerized risk management system of claim 32 wherein said warning means comprises a light signifying to the health care professional that the important factors have been documented with respect to the diagnosis or treatment of the patient.

34. The computerized risk management system of claim 32 wherein said warning means comprises a light signifying to the health care professional that the important factors have not been fully documented with respect to the diagnosis or treatment of the patient.

35. The computerized risk management system of claim 31 wherein the medical risk database includes data collected from medical malpractice claims.

36. The computerized risk management system of claim 31 wherein the patient data includes symptoms, medical history and personal data.

37. The computerized risk management system of claim 31 which further comprises means for the health care professional to retrieve preexisting patient data.

38. The computerized risk management system of claim 31 wherein the means to connect the data input means is a data link.

39. The computerized risk management system of claim 38 wherein the data link is an Internet connection.

40. The computerized risk management system of claim 38 wherein the data link is a wireless connection.

41. The computerized risk management system of claim 31 which further comprises means to provide the health care professional with a timed reminder to check on the patient.

42. The computerized risk management system of claim 31 which further comprises means to provide additional information to the health care professional about the illness, disease or injury.

43. The computerized risk management system of claim 31 which further comprises means to prioritize the patient with respect to other patients based on the inputted patient information.

44. The computerized risk management system of claim 43 which further comprises means to provide a warning of a high-risk diagnosis of an acute emergency.

45. The computerized risk management system of claim 31 which further comprises means to provide a template for the health care professional to input the patient information.

46. The computerized risk management system of claim 45 which further comprises means to provide a template comprising a series of queries.

47. The computerized risk management system of claim 46 which further comprises means to provide a plurality of additional queries based on responses to the series of queries.

48. The computerized risk management system of claim 47 which further includes means to indicate other information was inputted.

49. The computerized risk management system of claim 46 which further comprises one or more lights to indicate when information has been inputted in response to the series of queries.

50. The computerized risk management system of claim 31 wherein said medical risk database further includes information concerning the risk of at least one of the following: incorrect or delayed diagnosis; or missed, incorrect or delayed treatment.

51. The computerized risk management system of claim 31 further comprising:
 means to determine that additional symptoms or other patient information should be recorded and requesting recordation of additional symptoms or patient information by presenting one or more queries to the health care professional, depending upon said association between said medical care information in said medical risk database and said recorded symptoms or other patient information; and,
 means for determining whether additional queries should be provided to the health care professional and automatically providing said additional queries to said health care professional, in response to said symptoms or other patient information being recorded, in an interactive fashion.

52. The computerized risk management system of claim 32 wherein said warning means comprises at least one indicator signifying to the health care professional that the important factors have been documented with respect to the diagnosis or treatment of the patient.

53. The computerized risk management system of claim 38 wherein the data link is an Intranet connection.

54. The computerized risk management system of claim 46 which further comprises one or more indicators to indicate when information has been inputted in response to the series of queries.

55. The system of claim 31 wherein the information contained in the database is designed to ensure that the healthcare professional meets the requisite standard of care in treating the patient, and the means for prompting the healthcare professional comprises means to ensure that the healthcare professional has satisfied and documented that the necessary standard of care was met in treating the patient.

56. A computerized medical chart system for improving the medical care of patients by communicating with a health care professional preparing a medical record in connection with recording diagnosis, symptoms, treatment or other patient information, and including important elements of the patient's medical condition, comprising:
 a medical risk database containing information regarding a plurality of illnesses, diseases and/or injuries, wherein the information contained in the database comprises factors that should be addressed in connection with the diagnosis and treatment of the patients to ensure that the healthcare professional meets the requisite standard of care;
 means for comparing the recorded symptoms or other patient information with the information stored in the medical risk database to determine whether there exists a risk of the patient having one or more of the plurality of illnesses, diseases or injuries;
 means for associating said recorded symptoms or other patient information with medical care where there exists an increased risk of a missed diagnosis or treatment with respect to said one or more of the plurality of illnesses, diseases or injuries in order to prevent wrong or delayed diagnosis;
 means for presenting medical care information to said health care professional that would reduce the risk of missing the diagnosis of or incorrectly treating one or more of the plurality of illnesses, diseases or injuries in the event that said recorded symptoms or other patient information is associated with one or more of the plurality of illnesses, diseases or injuries; and,
 means for prompting the health care professional to, if necessary, take particular actions and include important items of said diagnosis, symptoms, treatment or other patient information in said medical record, wherein the means for prompting the healthcare professional comprises means to ensure that the healthcare professional has satisfied and documented that the necessary standard of care was met in treating the patient and wherein the means for prompting the healthcare professional to include the important items of the diagnosis, symptoms, treatment or other patient information comprises one or more red and green lights, wherein the lights will remain red until the healthcare professional inputs the necessary documentation into the system, wherein the lights will change to green.

57. A method for improving the medical care of patients by using a computerized medical chart creation system for communicating with a health care professional preparing a medical record in connection with recording diagnosis, symptoms, treatment or other patient information, and including important elements of the patient's medical condition, the computerized medical chart creation system including a medical risk database having information on a plurality of illnesses, diseases and/or injuries, wherein the information contained in the database comprises factors that should be addressed in connection with the diagnosis and treatment of the patients to ensure that the health care professional meets the requisite standard of care, the method comprising the steps of:
 recording said symptoms or other patient information;
 comparing said recorded symptoms or other patient information with the information stored in the medical risk database to determine whether there exists an increased risk that said patient may have one or more of said plurality of illnesses, diseases or injuries;
 presenting medical care information to said health care professional that would reduce the risk of missing the diagnosis of or incorrectly treating of said one or more of the plurality of illnesses, diseases or injuries in the event the recorded symptoms or other patient information it associated with the risk that the patient may have one or more of said plurality of illnesses, diseases or injuries; and
 prompting the health care professional to, if necessary, take particular actions and include important items of said diagnosis, symptoms, treatment or other patient information in said medical record, wherein the step of prompting the healthcare professional comprises means to ensure that the healthcare professional has satisfied and documented that the necessary standard of care was met in treating the patient and wherein the step of prompting the healthcare professional to include the important items of the diagnosis, symptoms, treatment or other patient information comprises one or more red and green lights, wherein the lights will remain red until the healthcare professional inputs the necessary documentation into the system, wherein the lights will change to green.

58. A computerized medical chart system for improving the medical care of patients by communicating with a healthcare professional preparing a medical record in connection with recording diagnosis, symptoms, treatment or other patient information, comprising:

- a medical risk database containing information regarding the treatment and diagnosis of a plurality of illnesses, diseases and/or injuries, wherein the information contained in the database comprises factors tat should be addressed in connection with the proper diagnosis and treatment of the patients to ensure that the healthcare professional meets the requisite standard of care in treating the patients;
- means for comparing the recorded symptoms or other patient information with the information stored in the medical risk database to determine whether there exists a risk of the patient having one or more of the plurality of illnesses, diseases or injuries;
- means for associating said recorded symptoms or other patient information with medical care where there exists an increased risk of a missed diagnosis or treatment with respect to said one or more of the plurality of illnesses, diseases or injuries in order to prevent wrong or delayed diagnosis; and
- means for prompting said healthcare professional to include important items of the diagnosis, symptoms, treatment or other patient information in said medical record to maintain a record of said healthcare professional's compliance wit said standard of care, wherein the means for prompting the healthcare professional to include the important elements of the patient's diagnosis, symptoms, treatment or other patient information comprises one or more red and green lights, wherein the lights will remain red until the healthcare professional inputs the necessary documentation into the system, wherein the lights will change to green.

59. A computerized risk management system for assisting a health care professional in diagnosing and treating possible illnesses, diseases or injuries of a patient associated with a computerized medical chart preparation system comprising:

- a medical risk database containing information regarding a plurality of illnesses, diseases and/or injuries, wherein the information contained in the database is designed to ensure that the healthcare professional meets the requisite standard of care in treating the patient;
- means to input data concerning the patient into a patient data record;
- a data processor, wherein the data processor compares the patient data in the patient data record with the information in the medical risk database to determine whether there is an increased risk of the patient having one or more of the illnesses, diseases or injuries;
- means to provide the health care professional with medical care information concerning the possible illnesses, diseases or injuries to reduce the possibility of the health care professional missing or erroneously treating the illnesses, diseases or injuries; and
- means to ensure that the healthcare professional has satisfied and documented that the necessary standard of care was met in treating the patient comprising one or more red and green lights, wherein the lights will remain red until the healthcare professional inputs the necessary patient data into the system, wherein the lights will change to green.

* * * * *

UNITED STATES PATENT AND TRADEMARK OFFICE
CERTIFICATE OF CORRECTION

| | |
|---|---|
| PATENT NO. | : 7,197,492 B2 |
| APPLICATION NO. | : 10/000879 |
| DATED | : March 27, 2007 |
| INVENTOR(S) | : Daniel Joseph Sullivan |

It is certified that error appears in the above-identified patent and that said Letters Patent is hereby corrected as shown below:

Column 2

Line 49, after "the" and before "of" insert --risk--

Column 4

Line 22, after "yet" and before "another" remove "is"
Line 29, after "yet" and before "another" remove "is"
Line 33, between "green" and "light" insert -- - --

Column 6

Line 14, after "joystick" and before "a" insert --,--

Column 7

Line 57, between "network" and "based" insert -- - --
Line 58, between "Internet" and "based" insert -- - --

Column 12

Line 1, replace "posses" with --poses--
Line 3, replace "Patient's" with --Patients--

Column 14

Line 53, replace "reevaluations" with --reevaluation--

Column 15

Line 6, replace "is it" with --it is--
Line 18, replace "collected" with --collecting--
Line 32, replace "imputing" with --inputting--
Line 34, after "P" and before ")" insert --"--
Line 64, replace "rather" with --further--

Column 17

Line 6, after "prevented" insert --the--

UNITED STATES PATENT AND TRADEMARK OFFICE
CERTIFICATE OF CORRECTION

PATENT NO. : 7,197,492 B2
APPLICATION NO. : 10/000879
DATED : March 27, 2007
INVENTOR(S) : Daniel Joseph Sullivan It is certified that error appears in the above-identified patent and that said Letters Patent is hereby corrected as shown below:

Column 19

Example 3, line 31, replace "or" with --of--
Example 3, line 39, replace "HX" with --Hx--

Column 20

Line 59, after "symptoms" and before "or" remove ","
Line 62, after "with" and before "the" remove ","

Column 21

Line 14, replace "fashiom" with --fashion--
Line 24, replace "associatedi" with --associated--
Line 32, replace "the" with --for--
Line 37, replace "dagnosis" with --diagnosis--
Line 53, replace "meas" with --means--

Column 22

Line 19, after "to" and before "medical" insert --the--
Line 46, after "injuries;" remove "and"

Column 23

Line 23, after "following" and before "incorrect" insert --:--
Line 64, replace "die" with --the--

Column 24

Line 3, remove "and"

Column 26

Line 59, after "it" and before "associated" insert --is--

UNITED STATES PATENT AND TRADEMARK OFFICE
CERTIFICATE OF CORRECTION

PATENT NO. : 7,197,492 B2
APPLICATION NO. : 10/000879
DATED : March 27, 2007
INVENTOR(S) : Daniel Joseph Sullivan It is certified that error appears in the above-identified patent and that said Letters Patent is hereby corrected as shown below:

Column 27

Line 17, after "," and before "wherein" insert a space
Line 18, replace "tat" with --that--
Line 38, replace "wit" with --with--

Signed and Sealed this

Seventeenth Day of July, 2007

JON W. DUDAS
*Director of the United States Patent and Trademark Office*